United States Patent
Christiano et al.

(10) Patent No.: US 10,138,258 B2
(45) Date of Patent: Nov. 27, 2018

(54) CYCLIC SILOXANE COMPOUNDS AND COMPOSITIONS COMPRISING THE SAME

(71) Applicant: Milliken & Company, Spartanburg, SC (US)

(72) Inventors: Steven P. Christiano, Spartanburg, SC (US); Olha V. Hoy, Greenville, SC (US); Megan J. Fresia, Greenville, SC (US); Nathaniel O. Hayes, Inman, SC (US); John G. Lever, Duncan, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 15/348,106

(22) Filed: Nov. 10, 2016

(65) Prior Publication Data

US 2017/0145148 A1    May 25, 2017

Related U.S. Application Data

(60) Provisional application No. 62/257,465, filed on Nov. 19, 2015.

(51) Int. Cl.
| | |
|---|---|
| *C07F 7/21* | (2006.01) |
| *C08G 59/14* | (2006.01) |
| *C08G 59/50* | (2006.01) |
| *C07F 7/08* | (2006.01) |

(52) U.S. Cl.
CPC .............. *C07F 7/21* (2013.01); *C07F 7/0812* (2013.01); *C08G 59/1438* (2013.01); *C08G 59/504* (2013.01)

(58) Field of Classification Search
CPC ........... C07F 7/21; C08G 77/26; C08G 77/80; C08L 83/00; C08L 83/04
USPC .............................................. 528/28, 37, 43
See application file for complete search history.

(56) References Cited

U.S. PATENT DOCUMENTS

| | | |
|---|---|---|
| 3,455,877 A | 7/1969 | Plueddemann |
| 4,208,503 A | 6/1980 | Martin |
| 4,245,079 A | 1/1981 | Natsumoto et al. |
| 4,892,918 A | 1/1990 | Ryang |
| 4,944,989 A | 7/1990 | Dorsch et al. |
| 5,037,861 A | 8/1991 | Crivello et al. |
| 5,153,332 A | 10/1992 | Enami et al. |
| 5,359,109 A | 10/1994 | Ritscher et al. |
| 5,378,790 A | 1/1995 | Michalczyk et al. |
| 6,005,131 A | 12/1999 | Jentsch et al. |
| 6,030,919 A | 2/2000 | Lewis |
| 6,624,236 B1 | 9/2003 | Bissinger et al. |
| 7,777,064 B2 | 8/2010 | Mizori |
| 8,008,419 B2 | 8/2011 | Dershem |
| 8,415,812 B2 | 4/2013 | Dershem et al. |
| 8,431,655 B2 | 4/2013 | Bershem |
| 8,513,375 B2 | 8/2013 | Mizori et al. |
| 8,541,531 B2 | 9/2013 | Dershem |
| 8,580,888 B2 | 11/2013 | Tully et al. |
| 9,006,307 B2 | 4/2015 | Iezzi et al. |
| 9,073,950 B2 | 7/2015 | Kownacka et al. |
| 2007/0205399 A1* | 9/2007 | Mizori ...................... C09J 5/00 252/500 |
| 2010/0041823 A1 | 2/2010 | Dershem |
| 2010/0249276 A1 | 9/2010 | Dershem |
| 2013/0228901 A1 | 9/2013 | Dershem et al. |

FOREIGN PATENT DOCUMENTS

| | | |
|---|---|---|
| EP | 1 207 163 A2 | 5/2002 |
| EP | 2 772 505 A1 | 9/2014 |
| JP | 10287715 | 10/1998 |
| JP | 5345880 | 11/2013 |
| WO | WO 2012/035112 A1 | 3/2012 |

OTHER PUBLICATIONS

PCT/US2016/061271 International Search Report, filed Nov. 10, 2016, 4 pages.
PCT/US2016/061271 Written Opinion of the International Searching Authority, filed Nov. 10, 2016, 4 pages.
Khananashvili, L.M. et al., Synthesis of Epoxycontaining Siliconorganic Compounds. Intern. J. Polymeric Mater., 1995, vol. 28. pp. 43-49.

* cited by examiner

*Primary Examiner* — Marc S Zimmer
(74) *Attorney, Agent, or Firm* — Robert M. Lanning

(57) ABSTRACT

A composition comprises a plurality of cyclic siloxane compounds. At least a portion of the cyclic siloxane compounds comprise first and second siloxane moieties having specified structures. A cyclic siloxane compound comprises a first siloxane moiety having a specified structure and a second siloxane moiety having a specified structure. An epoxy composition is made by reacting a composition comprising a plurality of cyclic siloxane compounds, an epoxy resin, and a curative. An epoxy composition is made by reacting a cyclic siloxane compound, an epoxy resin, and a curative.

19 Claims, No Drawings

CYCLIC SILOXANE COMPOUNDS AND COMPOSITIONS COMPRISING THE SAME

CROSS REFERENCE TO RELATED APPLICATIONS

This application claims, pursuant to 35 U.S.C. § 119(e)(1), priority to and the benefit of the filing date of U.S. Patent Application No. 62/257,465 filed on Nov. 19, 2015 which application is hereby incorporated by reference in its entirety.

TECHNICAL FIELD OF THE INVENTION

This application relates to compositions comprising cyclic siloxane compounds. More specifically, in certain embodiments, the compositions comprise cyclic siloxane compounds having functional groups that allow the compounds to react in epoxy systems. The application also relates to epoxy compositions made with such cyclic siloxane compounds.

BACKGROUND

Siloxane compounds are well known for their thermal stability, ability to maintain flexibility at low temperatures, and ability to impart hydrophobicity to surfaces. Therefore, it is not surprising that some have proposed incorporating siloxane compounds into epoxy systems. These solutions have been proposed as a means to reduce brittleness and increase hydrophobicity of the epoxy systems. While such solutions have been proposed, these solutions have not been without their problems. Siloxane compounds generally are not miscible in epoxy resin systems. Therefore, it is possible for a siloxane compound to phase separate from an epoxy system to which it is added. If such phase separation occurs, it can lead to defects in the cured epoxy.

A need therefore remains for siloxane compounds that are capable of reacting with epoxy resins and show improved compatibility with or solubility in a range of epoxy systems. A need also remains for epoxy products made by reacting such a siloxane compound with an epoxy resin. The invention described herein attempts to meet such needs.

BRIEF SUMMARY OF THE INVENTION

In a first embodiment, the invention provides a composition comprising a plurality of cyclic siloxane compounds, at least a portion of the cyclic siloxane compounds comprising a first siloxane moiety and a second siloxane moiety, wherein:
(a) the first siloxane moiety is selected from the group consisting of moieties conforming to the structure of Formula (I)

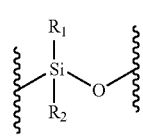

(I)

where $R_1$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups, and $R_2$ is a group comprising a cyclic ether moiety;
(b) the second siloxane moiety is selected from the group consisting of moieties conforming to the structure of Formula (X)

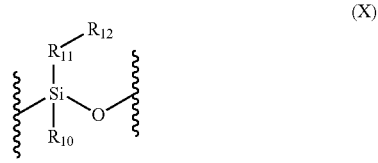

(X)

where $R_{10}$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups; $R_{11}$ is selected from the group consisting of alkanediyl groups and alkenediyl groups; and $R_{12}$ is selected from the group consisting of aryl groups, substituted aryl groups, heteroaryl groups, and substituted heteroaryl groups; and
(c) about 35% or more of the cyclic siloxane compounds present in the composition comprise at least one first siloxane moiety and at least one second siloxane moiety.

In a second embodiment, the invention provides a cyclic siloxane compound comprising a plurality of siloxane moieties, the compound comprising:
(a) at least one first siloxane moiety conforming to the structure of Formula (C)

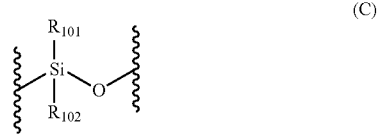

(C)

wherein $R_{101}$ is selected from the group consisting of alkyl groups; and $R_{102}$ is a group comprising a cyclic ether moiety; and
(b) at least one second siloxane moiety conforming to the structure of Formula (CX)

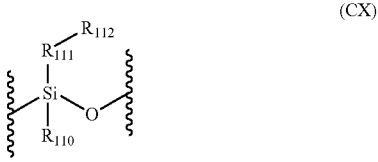

(CX)

wherein $R_{110}$ is selected from the group consisting of alkyl groups; $R_{111}$ is selected from the group consisting of alkanediyl groups and alkenediyl groups; and $R_{112}$ is selected from the group consisting of aryl groups and heteroaryl groups.

In a third embodiment, the invention provides an epoxy composition produced by reacting:

(a) a composition comprising a plurality of cyclic siloxane compounds, at least a portion of the cyclic siloxane compounds comprising a first siloxane moiety and a second siloxane moiety, wherein:

(i) the first siloxane moiety is selected from the group consisting of moieties conforming to the structure of Formula (I)

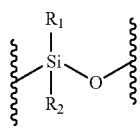

(I)

where $R_1$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups, and $R_2$ is a group comprising a cyclic ether moiety;

(ii) the second siloxane moiety is selected from the group consisting of moieties conforming to the structure of Formula (X)

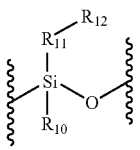

(X)

where $R_{10}$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups; $R_{11}$ is selected from the group consisting of alkanediyl groups and alkenediyl groups; and $R_{12}$ is selected from the group consisting of aryl groups, substituted aryl groups, heteroaryl groups, and substituted heteroaryl groups; and (iii) about 35% or more of the cyclic siloxane compounds present in the composition comprise at least one first siloxane moiety and at least one second siloxane moiety;

(b) an epoxy resin; and (c) a curative.

In a fourth embodiment, the invention provides an epoxy composition produced by reacting:

(a) a cyclic siloxane compound, the cyclic siloxane compound comprising:

(ii) at least one first siloxane moiety conforming to the structure of Formula (C)

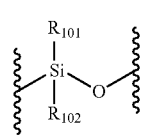

(C)

wherein $R_{101}$ is selected from the group consisting of alkyl groups; and $R_{102}$ is a group comprising a cyclic ether moiety; and (ii) at least one second siloxane moiety conforming to the structure of Formula (CX)

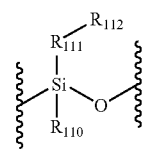

(CX)

wherein $R_{110}$ is selected from the group consisting of alkyl groups; $R_{111}$ is selected from the group consisting of alkanediyl groups and alkenediyl groups; and $R_{112}$ is selected from the group consisting of aryl groups and heteroaryl groups;

(b) an epoxy resin; and (c) a curative.

DETAILED DESCRIPTION OF THE INVENTION

The following definitions are provided to define several of the terms used throughout this application.

As used herein, the term "substituted alkyl groups" refers to univalent functional groups derived from substituted alkanes by removal of a hydrogen atom from a carbon atom of the alkane. In this definition, the term "substituted alkanes" refers to compounds derived from acyclic unbranched and branched hydrocarbons in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom (as in an ether), a nitrogen atom (as in an amine), or a sulfur atom (as in a sulfide).

As used herein, the term "substituted cycloalkyl groups" refers to univalent functional groups derived from substituted cycloalkanes by removal of a hydrogen atom from a carbon atom of the cycloalkane. In this definition, the term "substituted cycloalkanes" refers to compounds derived from saturated monocyclic and polycyclic hydrocarbons (with or without side chains) in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom, a nitrogen atom, or a sulfur atom.

As used herein, the term "alkenyl groups" refers to univalent functional groups derived from acyclic, unbranched and branched olefins (i.e., hydrocarbons having one or more carbon-carbon double bonds) by removal of a hydrogen atom from a carbon atom of the olefin.

As used herein, the term "substituted alkenyl groups" refers to univalent functional groups derived from acyclic, substituted olefins by removal of a hydrogen atom from a carbon atom of the olefin. In this definition, the term "substituted olefins" refers to compounds derived from acyclic, unbranched and branched hydrocarbons having one or more carbon-carbon double bonds in which (1) one or more of the hydrogen atoms of the hydrocarbon is replaced with a non-hydrogen atom (e.g., a halogen atom) or a non-alkyl functional group (e.g., hydroxy group, aryl group, heteroaryl group) and/or (2) the carbon-carbon chain of the hydrocarbon is interrupted by an oxygen atom (as in an ether) or a sulfur atom (as in a sulfide).

As used herein, the term "cycloalkenyl groups" refers to univalent functional groups derived from cyclic olefins (i.e., non-aromatic, monocyclic and polycyclic hydrocarbons having one or more carbon-carbon double bonds) by removal of a hydrogen atom from a carbon atom of the olefin. The carbon atoms in the cyclic olefins can be substituted with alkyl groups and/or alkenyl groups.

As used herein, the term "substituted cycloalkenyl groups" refers to univalent functional groups derived from substituted cyclic olefins by removal of a hydrogen atom from a carbon atom of the cyclic olefin. In this definition, the term "substituted cyclic olefins" refers to compounds derived from non-aromatic, monocyclic and polycyclic hydrocarbons having one or more carbon-carbon double bonds in which one or more of the hydrogen atoms of the hydrocarbon is replaced with a non-hydrogen atom (e.g., a halogen atom) or a non-alkyl functional group (e.g., hydroxy group, aryl group, heteroaryl group).

As used herein, the term "heterocyclyl groups" refers to univalent functional groups derived from heterocyclic compounds by removal of a hydrogen atom from an atom in the cyclic portion of the heterocyclic compound. In this definition, the term "heterocyclic compounds" refers to compounds derived from non-aromatic, monocyclic and polycyclic compounds having a ring structure composed of atoms of at least two different elements. These heterocyclic compounds can also comprise one or more double bonds.

As used herein, the term "substituted heterocyclyl groups" refers to univalent functional groups derived from substituted heterocyclic compounds by removal of a hydrogen atom from an atom in the cyclic portion of the compound. In this definition, the term "substituted heterocyclic compounds" refers to compounds derived from non-aromatic, monocyclic and polycyclic compounds having a ring structure composed of atoms of at least two different elements where one or more of the hydrogen atoms of the cyclic compound is replaced with a non-hydrogen atom (e.g., a halogen atom) or a functional group (e.g., hydroxy group, alkyl group, aryl group, heteroaryl group). These substituted heterocyclic compounds can also comprise one or more double bonds.

As used herein, the term "substituted aryl groups" refers to univalent functional groups derived from substituted arenes by removal of a hydrogen atom from a ring carbon atom. In this definition, the term "substituted arenes" refers to compounds derived from monocyclic and polycyclic aromatic hydrocarbons in which one or more of the hydrogen atoms of the hydrocarbon is replaced with a non-hydrogen atom (e.g., a halogen atom) or a non-alkyl functional group (e.g., hydroxy group).

As used herein, the term "substituted heteroaryl groups" refers to univalent functional groups derived from substituted heteroarenes by removal of a hydrogen atom from a ring carbon atom. In this definition, the term "substituted arenes" refers to compounds derived from monocyclic and polycyclic aromatic hydrocarbons in which (1) one or more of the hydrogen atoms of the hydrocarbon is replaced with a non-hydrogen atom (e.g., a halogen atom) or a non-alkyl functional group (e.g., hydroxy group) and (2) at least one methine group (—C=) of the hydrocarbon is replaced by a trivalent heteroatom and/or at least one vinylidene group (—CH=CH—) of the hydrocarbon is replaced by a divalent heteroatom.

As used herein, the term "alkanediyl groups" refers to divalent functional groups derived from alkanes by removal of two hydrogen atoms from the alkane. These hydrogen atoms can be removed from the same carbon atom on the alkane (as in ethane-1,1-diyl) or from different carbon atoms (as in ethane-1,2-diyl).

As used herein, the term "substituted alkanediyl groups" refers to divalent functional groups derived from substituted alkanes by removal of two hydrogen atoms from the alkane. These hydrogen atoms can be removed from the same carbon atom on the substituted alkane (as in 2-fluoroethane-1,1-diyl) or from different carbon atoms (as in 1-fluoroethane-1,2-diyl). In this definition, the term "substituted alkanes" has the same meaning as set forth above in the definition of substituted alkyl groups.

As used herein, the term "alkenediyl groups" refers to divalent functional groups derived from acyclic, unbranched and branched olefins (i.e., hydrocarbons having one or more carbon-carbon double bonds) by removal of two hydrogen atoms from the olefin. These hydrogen atoms can be removed from the same carbon atom on the olefin (as in but-2-ene-1,1-diyl) or from different carbon atoms (as in but-2-ene-1,4-diyl).

As used herein, the term "acyl groups" refers to univalent functional groups derived from alkyl carboxylic acids by removal of a hydroxy group from a carboxylic acid group. In this definition, the term "alkyl carboxylic acids" refers to acyclic, unbranched and branched hydrocarbons having one or more carboxylic acid groups.

As used herein, the term "substituted acyl groups" refers to univalent functional groups derived from substituted alkyl carboxylic acids by removal of a hydroxy group from a carboxylic acid group. In this definition, the term "substituted alkyl carboxylic acids" refers to compounds having one or more carboxylic acid groups bonded to a substituted alkane, and the term "substituted alkane" is defined as it is above in the definition of substituted alkyl groups.

As used herein, the term "siloxy groups" refers to univalent functional groups having the structure —[OSi$R_xR_y$]$_w$$R_z$, where $R_x$, $R_y$, and $R_z$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, substituted heteroaryl groups and the variable w is an integer equal to or greater than 1. In a preferred embodiment, $R_x$, $R_y$, and $R_z$ are independently selected from the group consisting of alkyl groups (e.g., $C_1$-$C_8$ alkyl groups), and the variable w is an integer from 1 to 50, more preferably 1 to 20.

In a first embodiment, the invention provides a composition comprising a plurality of cyclic siloxane compounds. Generally, the cyclic siloxane compounds comprise three or more siloxane moieties. The silicon atoms in these siloxane moieties can be substituted with any suitable functional groups. The cyclic siloxane compounds can comprise any suitable combination of different siloxane moieties. Further, the composition generally comprises a mixture of several different cyclic siloxane compounds. These different cyclic siloxane compounds differ in the number of siloxane moieties in the compound (e.g., 3, 4, 5, or more siloxane moieties) and/or the functional groups attached to the silicon atoms in the siloxane moieties.

Preferably, at least a portion of the cyclic siloxane compounds present in the composition comprise a first siloxane moiety and a second siloxane moiety. In such an embodiment, the first siloxane moiety is selected from the group consisting of moieties conforming to the structure of Formula (I) below

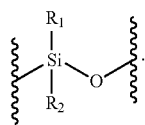
(I)

In the structure of Formula (I), $R_1$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups. $R_2$ is a group comprising a cyclic ether moiety. In this same embodiment, the second siloxane moiety preferably is selected from the group consisting of moieties conforming to the structure of Formula (X) below

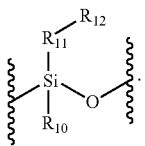
(X)

In the structure of Formula (X), $R_{10}$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups. $R_{11}$ is selected from the group consisting of alkanediyl groups and alkenediyl groups. $R_{12}$ is selected from the group consisting of aryl groups, substituted aryl groups, heteroaryl groups, and substituted heteroaryl groups.

The structure of Formula (IA) below depicts an exemplary structure for a cyclic siloxane compound comprising at least one first siloxane moiety and at least one second siloxane moiety as described above. The structure of Formula (IA) is

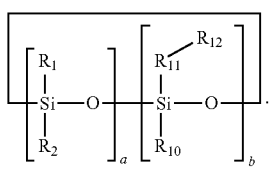
(IA)

In the structure of Formula (IA), each $R_1$, $R_2$, $R_{10}$, $R_{11}$, and $R_{12}$ is independently selected from the same groups recited above for the structures of Formula (I) and Formula (X). The variable a denotes the number of first siloxane moieties present in the cyclic siloxane compound and is selected from the group consisting of positive integers equal to or greater than 1. The variable b denotes the number of second siloxane moieties present in the cyclic siloxane compound and is selected from the group consisting of positive integers equal to or greater than 1. Preferably, the sum of the variables a and b is 3 or more, more preferably 4 or more. In another preferred embodiment, the sum of the variables a and b is 10 or less, more preferably 8 or less, most preferably 6 or less (e.g., 5 or less). For the sake of simplicity, the structure of Formula (IA) depicts the cyclic siloxane compound in a block configuration, with siloxane moieties having the same structure grouped together in the cyclic siloxane compound. The cyclic siloxane can have such a block configuration. However, more commonly, the cyclic siloxane compound will have a random configuration, in which the different siloxane moieties are randomly arranged in each molecule of the cyclic siloxane compound. The structure of Formula (IA) is intended to encompass and serve as a schematic representation of the structure of both types of compounds—the block configuration and the random configuration.

In the structures of Formula (I) and Formula (IA), $R_1$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups. In a preferred embodiment, $R_1$ is selected from the group consisting of alkyl groups, with $C_1$-$C_8$ alkyl groups being particularly preferred. For example, in a preferred embodiment, $R_1$ is a methyl group.

As noted above, in the structures of Formula (I) and (IA), $R_2$ is a group comprising a cyclic ether moiety. The cyclic ether moiety can comprise any suitable number of atoms, such as the three-membered epoxide moiety, a four-membered oxetanyl moiety, a five-membered tetrahydrofuranyl moiety, or a six-membered tetrahydropyranyl moiety. In a preferred embodiment, $R_2$ comprises an epoxide moiety. Further, the $R_2$ group can comprise any suitable linear or cyclic moiety attached to the cyclic ether moiety. For example, the $R_2$ group can comprise an alkanediyl moiety bonded to the cyclic ether moiety, such as in a glycidyl group (2,3-epoxypropyl group). Alternatively, the $R_2$ group can comprise a cyclic moiety forming a fused ring system with the cyclic ether moiety, such as in a 3,4-epoxycyclohexyl group. In a preferred embodiment, $R_2$ is selected from the group consisting of 5,6-epoxyhexyl and 2-(3,4-epoxycyclohexyl)ethyl. In another preferred embodiment, $R_2$ is a group conforming to the structure —$R_5$—O—$R_6$, where $R_5$ is an alkanediyl group and $R_6$ is a group comprising an epoxide moiety. In a preferred embodiment, $R_5$ is a propane-1,3-diyl group, and $R_6$ is a glycidyl group.

In the structures of Formula (X) and (IA), $R_{10}$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups. In a preferred embodiment, $R_{10}$ is selected from the group consisting of alkyl groups, with $C_1$-$C_8$ alkyl groups being particularly preferred. For example, in a preferred embodiment, $R_{10}$ is a methyl group.

In the structures of Formula (X) and (IA), $R_{11}$ is selected from the group consisting of alkanediyl groups and alkenediyl groups. $C_1$-$C_8$ alkanediyl groups and $C_1$-$C_8$ alkenediyl groups are preferred, but other suitable alkanediyl and alkenediyl groups can be present. In a preferred embodiment, $R_{11}$ is a $C_1$-$C_8$ alkanediyl group, one preferred example of which is 2-methylethane-1,2-diyl.

In the structures of Formula (X) and (IA), $R_{12}$ is selected from the group consisting of aryl groups, substituted aryl groups, heteroaryl groups, and substituted heteroaryl groups. In a preferred embodiment, $R_{12}$ is selected from the group consisting of $C_6$-$C_{10}$ aryl groups, one preferred example of which is a phenyl group.

Thus, in a preferred embodiment, $R_1$ is an alkyl group (preferably a $C_1$-$C_8$ alkyl group), and $R_2$ is a group comprising an epoxide moiety. In another preferred embodiment, $R_{10}$ is an alkyl group (preferably a $C_1$-$C_8$ alkyl group), $R_{11}$ is an alkanediyl group (preferably a $C_1$-$C_8$ alkanediyl group), and $R_{12}$ is an aryl group (preferably a $C_6$-$C_{10}$ aryl group). Thus, in one particular preferred embodiment, $R_1$ is an alkyl group (preferably a $C_1$-$C_8$ alkyl group), $R_2$ is a group comprising an epoxide moiety, $R_{10}$ is an alkyl group (preferably a $C_1$-$C_8$ alkyl group), $R_{11}$ is an alkanediyl group (preferably a $C_1$-$C_8$ alkanediyl group), and $R_{12}$ is an aryl group (preferably a $C_6$-$C_{10}$ aryl group). In a more specific preferred embodiment, $R_1$ is a methyl group, $R_2$ is a group conforming to the structure of —$R_5$—O—$R_6$, $R_5$ is a propane-1,3-diyl group, $R_6$ is a glycidyl group, $R_{10}$ is a methyl group, $R_{11}$ is a 2-methylethane-1,2-diyl group, and $R_{12}$ is a phenyl group.

As noted above, the composition can comprise a mixture of different cyclic siloxane compounds. This mixture can result from the process used to produce the composition, an example of which is described in detail below. Thus, in a composition containing cyclic siloxane compounds comprising the first and second siloxane moieties described above, the composition can also contain cyclic siloxane compounds containing only first siloxane moieties as well as cyclic siloxane compounds containing only second siloxane moieties. A cyclic siloxane compound containing only first siloxane moieties will conform to the structure of Formula (IZ) below:

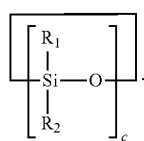

(IZ)

In the structure of Formula (IZ), each $R_1$ and $R_2$ is independently selected from the various groups recited above for the structure of Formula (I). The variable c is a positive integer equal to or greater than 3. Preferably, the variable c is 10 or less, more preferably 8 or less, and most preferably 6 or less. A cyclic siloxane compound containing only second siloxane moieties will conform to the structure of Formula (XA) below:

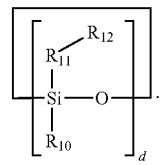

(XA)

In the structure of Formula (XA), each $R_{10}$, $R_{11}$, and $R_{12}$ is independently selected from the various groups recited above for the structure of Formula (X). The variable d is a positive integer equal to or greater than 3. Preferably, the variable d is 10 or less, more preferably 8 or less, and most preferably 6 or less.

Preferably, the composition does not contain an excessive amount of cyclic siloxane compounds comprising only first siloxane moieties or an excessive amount of cyclic siloxane compounds comprising only second siloxane moieties. For example, in a preferred embodiment, about 20% or less of the cyclic siloxane compounds present in the composition contain only first siloxane moieties. In other words, in such preferred embodiment, about 20% or less of the cyclic siloxane compounds present in the composition conform to the structure of Formula (IZ) above. In another preferred embodiment, about 10% or less of the cyclic siloxane compounds present in the composition contain only second siloxane moieties. In other words, in such preferred embodiment, about 10% or less of the cyclic siloxane compounds present in the composition conform to the structure of Formula (XA).

In another preferred embodiment, about 35% or more of the cyclic siloxane compounds present in the composition comprise at least one first siloxane moiety (i.e., a moiety conforming to the structure of Formula (I) above) and at least one second siloxane moiety (i.e., a moiety conforming to the structure of Formula (X) above). Thus, in such a preferred embodiment, about 35% or more of the cyclic siloxane compounds present in the composition conform to the structure of Formula (IA) above. More preferably, about 40% or more, about 45% or more, about 50% or more, about 55% or more, about 60% or more, about 65% or more, about 70% or more, or about 75% or more of the cyclic siloxane compounds present in the composition comprise at least one first siloxane moiety and at least one second siloxane moiety (and therefore conform to the structure of Formula (IA) above).

The cyclic siloxane compounds present in the composition can contain any suitable ratio of first siloxane moieties (i.e., moieties conforming to the structure of Formula (I)) and second siloxane moieties (i.e., moieties conforming to the structure of Formula (X)). Preferably, the ratio of first siloxane moieties to second siloxane moieties is about 1:9 or more. More preferably, the ratio of first siloxane moieties to second siloxane moieties is about 1:4 or more, about 1:3 or more, about 3:7 or more, about 1:2 or more, about 4:7 or more, about 3:5 or more, about 4:5 or more, or about 1:1 or more. Preferably, the ratio of first siloxane moieties to second siloxane moieties is about 9:1 or less. More preferably, the ratio of first siloxane moieties to second siloxane moieties is about 4:1 or less, about 3:1 or less, about 7:3 or less, about 2:1 or less, about 7:4 or less, or about 5:3 or less. Thus, in a series of preferred embodiments, the ratio of first siloxane moieties to second siloxane moieties is about 1:9 to about 9:1, about 1:4 to about 4:1, about 1:3 to about 3:1, about 3:7 to about 7:3, about 1:2 to about 2:1, about 4:7 to about 7:4, or about 3:5 to about 5:3. In another preferred embodiment, the ratio of first siloxane moieties to second siloxane moieties is about 4:5 to about 7:4, more preferably about 1:1 to about 7:4 (e.g., about 1:1 to about 5:3). The ratios of first siloxane moieties to second siloxane moieties in the cyclic siloxane compounds described above represent averages for the population or collection of molecules of cyclic siloxane compounds within the composition described above. Thus, individual molecules within the composition may possess ratios of first and second siloxane moieties falling outside of these ratios. However, when the ratios for such individual molecules are averaged with the ratios for all of the other molecules within the composition, the average ratio for the entire population or collection of molecules within the composition preferably falls within one of the ranges described above.

As noted above, the cyclic siloxane compounds contained in the composition can contain any suitable number of siloxane moieties. Generally, the cyclic siloxane compounds comprise three or more siloxane moieties. In a preferred embodiment, about 90% or more of the cyclic siloxane compounds present in the composition contain four siloxane moieties or five siloxane moieties.

In certain embodiments, the cyclic siloxane compounds present in the composition can comprise siloxane moieties other than the first and second siloxane moieties described above. For example, the cyclic siloxane compound can comprise at least one siloxane moiety conforming to the structure of Formula (V) below

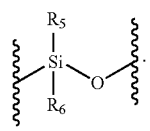

(V)

In the structure of Formula (V), $R_5$ and $R_6$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups. In a preferred embodiment, $R_5$ and $R_6$ are selected from the group consisting of alkyl groups, with $C_1$-$C_{20}$ alkyl groups being particularly preferred. For example, in a preferred embodiment, one of $R_5$ and $R_6$ is a $C_1$-$C_8$ alkyl group, preferably a methyl group, and one of $R_5$ and $R_6$ is a $C_{10}$-$C_{20}$ alkyl group (e.g., a $C_{12}$ alkyl group). When the cyclic siloxane compound contains a siloxane moiety conforming to the structure of Formula (V), the total number of siloxane moieties in the cyclic siloxane compound still preferably falls within one of the ranges described above.

In certain preferred embodiments, the composition contains only a limited amount of cyclic siloxane compounds comprising one or more silanol (—Si—OH) groups. Preferably, about 40% or less of the cyclic siloxane compounds present in the composition contain one or more silanol groups. More preferably, about 35% or less, about 30% or less, about 25% or less, about 20% or less, about 15% or less, about 10% or less, or about 5% or less of the cyclic siloxane compounds present in the composition contain one or more silanol groups. Most preferably, less than 1% (e.g., about 0.5% or less) of the cyclic siloxane compounds present in the composition contain one or more silanol groups.

The composition described above can contain other siloxane compounds in addition to the cyclic siloxane compounds described above. For example, the composition can comprise linear or acyclic siloxane compounds. In a preferred embodiment, the composition comprises one or more acyclic siloxane compounds conforming to the structure of Formula (L) below

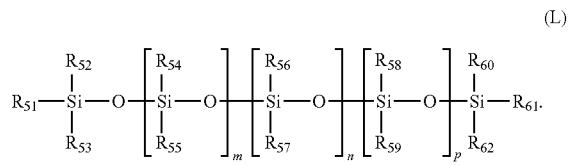

(L)

In the structure of Formula (L), $R_{51}$, $R_{52}$, $R_{53}$, $R_{54}$, $R_{55}$, $R_{56}$, $R_{57}$, $R_{58}$, $R_{59}$, $R_{60}$, $R_{61}$, and $R_{62}$ are independently selected from the group consisting of alkyl groups, siloxy groups, and $R_2$. The group $R_2$ is the same as the group discussed in connection with the structure of Formula (I) above. More preferably, $R_{51}$, $R_{52}$, $R_{53}$, $R_{60}$, $R_{61}$, and $R_{62}$ are independently selected from the group consisting of alkyl groups, and $R_{54}$, $R_{55}$, $R_{56}$, $R_{57}$, $R_{58}$, and $R_{59}$ are independently selected from the group consisting of alkyl groups, siloxy groups, and $R_2$. Preferably, the alkyl groups are selected from the group consisting of $C_1$-$C_8$ alkyl groups, more preferably $C_1$-$C_4$ alkyl groups, and most preferably methyl groups. Preferably, the siloxy groups are trimethylsiloxy groups. The variables m, n, and p are independently selected from the group consisting of integers from 0 to 5, more preferably integers from 0 to 3. The sum of the variables m, n, and p preferably is from 1 to 5, more preferably from 1 to 3. Preferably, at least one of $R_{51}$, $R_{52}$, $R_{53}$, $R_{54}$, $R_{55}$, $R_{56}$, $R_{57}$, $R_{58}$, $R_{59}$, $R_{60}$, $R_{61}$, and $R_{62}$ is an $R_2$ group. More preferably, at least one of $R_{54}$, $R_{55}$, $R_{56}$, $R_{57}$, $R_{58}$, and $R_{59}$ is an $R_2$ group. In such an embodiment, the remaining groups preferably are alkyl groups, more preferably methyl groups.

If present in the composition, the acyclic siloxane compound(s) can be present in any suitable amount. While not wishing to be bound to any particular theory, it is believed that the presence of the acyclic siloxane compound(s) helps to control the viscosity of the composition, making it suitable for handling and incorporation into an epoxy resin composition, as discussed below. Accordingly, the amount of acyclic siloxane compound(s) present in the composition can depend, at least in part, on the desired viscosity of the composition. Preferably, the acyclic siloxane compounds(s) are present in the composition in an amount of about 1% or more of the molar amount of cyclic siloxane compounds present in the composition. In another preferred embodiment, the acyclic siloxane compound(s) are present in the composition in an amount of about 5% or more, about 6% or more, about 7% or more, or about 8% or more of the molar amount of cyclic siloxane compounds present in the composition. Preferably, the acyclic siloxane compound(s) are present in the composition in an amount of about 20% or less of the molar amount of cyclic siloxane compounds present in the composition.

In a second embodiment, the invention provides a cyclic siloxane compound comprising a plurality of siloxane moieties. The cyclic siloxane compound comprises at least one first siloxane moiety conforming to the structure of Formula (C) below

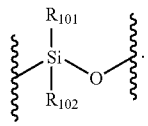
(C)

In the structure of Formula (C), $R_{101}$ is selected from the group consisting of alkyl groups, and $R_{102}$ is a group comprising a cyclic ether moiety. The cyclic siloxane compound also comprises at least one second siloxane moiety conforming to the structure of Formula (CX) below

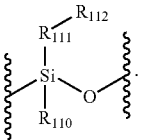
(CX)

In the structure of Formula (CX), $R_{110}$ is selected from the group consisting of alkyl groups, $R_{111}$ is selected from the group consisting of alkanediyl groups and alkenediyl groups, and $R_{112}$ is selected from the group consisting of aryl groups and heteroaryl groups.

The structure of Formula (CA) below depicts an exemplary structure for a cyclic siloxane compound comprising at least one first siloxane moiety conforming to the structure of Formula (C) and at least one second siloxane moiety conforming to the structure of Formula (CX) as described above. The structure of Formula (CA) is

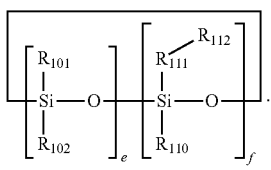
(CA)

In the structure of Formula (CA), each $R_{101}$, $R_{102}$, $R_{110}$, $R_{111}$, and $R_{112}$ is independently selected from the same groups recited above for the structure of Formula (C) and (CX). The variable e denotes the number of first siloxane moieties conforming to the structure of Formula (C) present in the cyclic siloxane compound. The variable e is selected from the group consisting of positive integers equal to or greater than 1. The variable f denotes the number of second siloxane moieties conforming to the structure of Formula (CX) present in the cyclic siloxane compound. The variable f is selected from the group consisting of positive integers equal to or greater than 1. Preferably, the sum of the variables e and f is 3 or more, more preferably 4 or more. In another preferred embodiment, the sum of the variables e and f is 10 or less, more preferably 8 or less, most preferably 6 or less (e.g., 5 or less). For the sake of simplicity, the structure of Formula (CA) depicts the cyclic siloxane compound in a block configuration, with siloxane moieties having the same structure grouped together in the cyclic siloxane compound. The cyclic siloxane can have such a block configuration. However, more commonly, the cyclic siloxane compound will have a random configuration, in which the different siloxane moieties are randomly arranged in each molecule of the cyclic siloxane compound. The structure of Formula (CA) is intended to serve as a schematic representation of the structure of both types of compounds—the block configuration and the random configuration.

In the structures of Formula (C) and (CA), $R_{101}$ is selected from the group consisting of alkyl groups. In a preferred embodiment of this cyclic siloxane compound, $R_{101}$ is selected from the group consisting of $C_1$-$C_8$ alkyl groups. In another preferred embodiment, $R_{101}$ is selected from the group consisting of $C_1$-$C_4$ alkyl groups, with a methyl group being particularly preferred.

In the structures of Formula (C) and (CA), $R_{102}$ is a group comprising a cyclic ether moiety. Suitable $R_{102}$ groups include all of those groups described above for $R_2$ in the first embodiment of the invention. In a preferred embodiment, $R_{102}$ comprises an epoxide moiety. In another preferred embodiment, $R_{102}$ is selected from the group consisting of 5,6-epoxyhexyl and 2-(3,4-epoxycyclohexyl)ethyl. In another preferred embodiment, $R_{102}$ is a group conforming to the structure —$R_5$—O—$R_6$, where $R_5$ is an alkanediyl group and $R_6$ is a group comprising an epoxide moiety. In a preferred example of such an embodiment, $R_5$ is a propane-1,3-diyl group, and $R_6$ is a glycidyl group.

In the structures of Formula (CX) and (CA), $R_{110}$ is selected from the group consisting of alkyl groups. In a preferred embodiment, $R_{110}$ is selected from the group consisting of $C_1$-$C_8$ alkyl groups. In another preferred embodiment, $R_{110}$ is selected from the group consisting of $C_1$-$C_4$ alkyl groups, with a methyl group being particularly preferred.

In the structures of Formula (CX) and (CA), $R_{111}$ is selected from the group consisting of alkanediyl groups and alkenediyl groups. In a preferred embodiment, $R_{111}$ is selected from the group consisting of $C_1$-$C_8$ alkanediyl groups and $C_1$-$C_8$ alkenediyl groups. More preferably, $R_{111}$ is selected from the group consisting of $C_1$-$C_4$ alkanediyl groups and $C_1$-$C_4$ alkenediyl groups. In another preferred embodiment, $R_{111}$ is 2-methylethane-1,2-diyl.

In the structures of Formula (CX) and (CA), $R_{112}$ is selected from the group consisting of aryl groups and heteroaryl groups. In a preferred embodiment, $R_{112}$ is selected from the group consisting of aryl groups. Preferably, $R_{112}$ is selected from the group consisting of $C_6$-$C_{10}$ aryl groups, one preferred example of which is a phenyl group.

Thus, in a preferred embodiment of this cyclic siloxane compound, $R_{101}$ is a $C_1$-$C_8$ alkyl group (preferably a $C_1$-$C_4$ alkyl group), and $R_{102}$ is a group comprising an epoxide moiety. In another preferred embodiment, $R_{110}$ is a $C_1$-$C_8$ alkyl group (preferably a $C_1$-$C_4$ alkyl group), $R_{111}$ is an alkanediyl group (preferably a $C_1$-$C_8$ alkanediyl group), and $R_{112}$ is an aryl group (preferably a $C_6$-$C_{10}$ aryl group). Thus, in one particular preferred embodiment, $R_{101}$ is a $C_1$-$C_8$ alkyl group (preferably a $C_1$-$C_4$ alkyl group), $R_{102}$ is a group comprising an epoxide moiety, $R_{110}$ is a $C_1$-$C_8$ alkyl group (preferably a $C_1$-$C_4$ alkyl group), $R_{111}$ is an alkanediyl group (preferably a $C_1$-$C_8$ alkanediyl group), and $R_{112}$ is an aryl group (preferably a $C_6$-$C_{10}$ aryl group). In a more specific preferred embodiment, $R_{101}$ is a methyl group, $R_{102}$ is a group conforming to the structure of —$R_5$—O—$R_6$, $R_5$ is a propane-1,3-diyl group, $R_6$ is a glycidyl group, $R_{110}$ is a methyl group, $R_{111}$ is a 2-methylethane-1,2-diyl group, and $R_{112}$ is a phenyl group.

The cyclic siloxane compound described above can contain any suitable ratio of first siloxane moieties (i.e., moieties conforming to the structure of Formula (C)) and second siloxane moieties (i.e., moieties conforming to the structure of Formula (CX)). Preferably, the ratio of first siloxane moieties to second siloxane moieties is about 1:9 or more. More preferably, the ratio of first siloxane moieties to second siloxane moieties is about 1:4 or more, about 1:3 or more, about 3:7 or more, about 1:2 or more, about 4:7 or more, about 3:5 or more, about 4:5 or more, or about 1:1 or more. Preferably, the ratio of first siloxane moieties to second siloxane moieties is about 9:1 or less. More preferably, the ratio of first siloxane moieties to second siloxane moieties is about 4:1 or less, about 3:1 or less, about 7:3 or less, about 2:1 or less, about 7:4 or less, or about 5:3 or less. Thus, in a series of preferred embodiments, the ratio of first siloxane moieties to second siloxane moieties is about 1:9 to about 9:1, about 1:4 to about 4:1, about 1:3 to about 3:1, about 3:7 to about 7:3, about 1:2 to about 2:1, about 4:7 to about 7:4, or about 3:5 to about 5:3. In another preferred embodiment, the ratio of first siloxane moieties to second siloxane moieties is about 4:5 to about 7:4, more preferably about 1:1 to about 7:4 (e.g., about 1:1 to about 5:3). The ratios of first siloxane moieties to second siloxane moieties in the cyclic siloxane compound described above represent averages for a population or collection of cyclic siloxane molecules. Thus, individual molecules within the population or collection may possess ratios of first and second siloxane moieties falling outside of these ratios. However, when the ratios for such individual molecules are averaged with the ratios for all of the other molecules within the population or collection, the average ratio for the entire population or collection of cyclic siloxane molecules preferably falls within one of the ranges described above.

The cyclic siloxane compound of this second embodiment can contain any suitable number of siloxane moieties. Generally, the cyclic siloxane compound comprises three or more siloxane moieties. In a preferred embodiment, the cyclic siloxane compound contains four siloxane moieties.

In certain embodiments, the cyclic siloxane compound of the second embodiment can comprise siloxane moieties other than the first and second siloxane moieties described above. For example, the cyclic siloxane compound can comprise at least one siloxane moiety conforming to the structure of Formula (CV) below

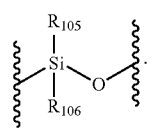

(CV)

In the structure of Formula (CV), $R_{105}$ and $R_{106}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups. In a preferred embodiment, $R_{105}$ and $R_{106}$ are selected from the group consisting of alkyl groups, with $C_1$-$C_{20}$ alkyl groups being particularly preferred. For example, in a preferred embodiment, one of $R_{105}$ and $R_{106}$ is a $C_1$-$C_8$ alkyl group, preferably a methyl group, and one of $R_{105}$ and $R_{106}$ is a $C_{10}$-$C_{20}$ alkyl group (e.g., a $C_{12}$ alkyl group). When the cyclic siloxane compound contains a siloxane moiety conforming to the structure of Formula (CV), the total number of siloxane moieties in the cyclic siloxane compound still preferably falls within one of the ranges described above.

The cyclic siloxane compound of the second embodiment can be present in a composition containing one or more additional siloxane compounds. For example, the composition containing the cyclic siloxane compound can comprise additional cyclic siloxane compounds, such as cyclic siloxane compounds containing only siloxane moieties conforming to the structure of Formula (C), cyclic siloxane compounds containing only siloxane moieties conforming to the structure of Formula (CX), and cyclic siloxane compound containing only siloxane moieties conforming to the structure of Formula (CV). The composition can also contain linear or acyclic siloxane compounds. In a preferred embodiment, this composition comprises the cyclic siloxane compound of the second embodiment and at least one acyclic siloxane compound conforming to the structure of Formula (L) as described above. In such an embodiment, the acyclic siloxane compound(s) can be present in the composition in any suitable amount. While not wishing to be bound to any particular theory, it is believed that the presence of the acyclic siloxane compound(s) helps to control the viscosity of the composition, making it suitable for handling and incorporation into an epoxy resin composition, as discussed below. Accordingly, the amount of acyclic siloxane compound(s) present in the composition can depend, at least in part, on the desired viscosity of the composition. Preferably, the acyclic siloxane compounds(s) are present in the composition in an amount of about 1% or more of the molar amount of cyclic siloxane compounds present in the composition. In another preferred embodiment, the acyclic siloxane compound(s) are present in the composition in an amount of about 5% or more, about 6% or more, about 7% or more, or about 8% or more of the molar amount of cyclic siloxane compounds present in the composition. Preferably, the acyclic siloxane compound(s) are present in the composition in an amount of about 20% or less of the molar amount of cyclic siloxane compounds present in the composition.

The composition of the first embodiment and the cyclic siloxane compound of the second embodiment can be produced by any suitable method or process. In one method, the composition and the cyclic siloxane compound are produced through the hydrosilylation of cyclic hydrosiloxanes with compounds comprising an acyclic, unsaturated carbon-carbon bond, such as an alkene or an alkyne.

In the hydrosilylation reaction described above, the cyclic hydrosiloxane compound comprises at least one siloxane moiety conforming to the structure of Formula (XX) below

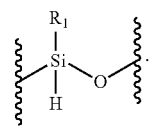

(XX)

In the structure of Formula (XX), $R_1$ is selected from the groups recited above in the description of the structure of Formula (I). The cyclic hydrosiloxane compound preferably comprises three or more (more preferably, four or more)

siloxane moieties conforming to the structure of Formula (XX). The structure of Formula (XXA) below depicts an exemplary structure of such a cyclic hydrosiloxane compound:

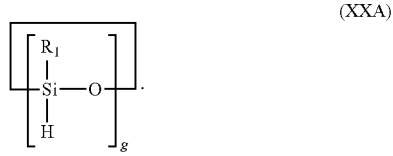

(XXA)

In the structure of Formula (XXA), each $R_1$ is independently selected from the groups recited above in the description of the structure of Formula (I). The variable g represent the number of siloxane moieties in the cyclic hydrosiloxane compound. The variable g is a positive integer equal to or greater than three. In this hydrosilylation reaction, more than one cyclic hydrosiloxane compound can be used. For example, the cyclic hydrosiloxane compound portion of the reactants can be a mixture of several different cyclic hydrosiloxanes comprising moieties conforming to the structure of Formula (XX), such as cyclic hydrotrisiloxanes, cyclic hydrotetrasiloxanes, cyclic hydropentasiloxanes, and cyclic hydrohexasiloxanes. Indeed, commercially available starting materials containing such cyclic hydrosiloxanes often are a mixture of different cyclic hydrosiloxane compounds. In addition, such starting materials can contain small amounts of acyclic hydrosiloxane compounds, but the content of such acyclic hydrosiloxane compounds preferably is relatively low in order to minimize undesirable side reactions and maximize the yield of cyclic siloxane compounds from the hydrosilylation reaction.

As noted above, the cyclic hydrosiloxane compound is reacted with a first compound comprising an acyclic, unsaturated carbon-carbon bond and a second compound comprising an acyclic, unsaturated carbon-carbon bond. The first compound comprising an acyclic, unsaturated carbon-carbon bond reacts with one of the siloxane moieties conforming to the structure of Formula (XX) to form a bond between the silicon atom in the siloxane moiety and a carbon atom in the acyclic, unsaturated carbon-carbon bond. This reaction yields a siloxane moiety conforming to the structure of Formula (X). In other words, the hydrogen in the siloxane moiety reacts with the first compound comprising an acyclic, unsaturated carbon-carbon bond to yield the —$R_{11}$-$R_{12}$ group in the structure of Formula (X). Thus, the first compound comprising an acyclic, unsaturated carbon-carbon bond can be any suitable alkene or alkyne compound that reacts with the hydrogen in the siloxane moiety to yield an —$R_{11}$-$R_{12}$ group selected from the groups recited above. The second compound comprising an acyclic, unsaturated carbon-carbon bond reacts with another of the siloxane moieties conforming to the structure of Formula (XX) to form a bond between the silicon atom in the siloxane moiety and a carbon atom in the acyclic, unsaturated carbon-carbon bond. This reaction yields a siloxane moiety conforming to the structure of Formula (I). In other words, the hydrogen in the siloxane moiety reacts with the second compound comprising an acyclic, unsaturated carbon-carbon bond to yield the $R_2$ group in the structure of Formula (I). Thus, the second compound comprising an acyclic, unsaturated carbon-carbon bond can be any suitable alkene or alkyne compound that reacts with the hydrogen in the siloxane moiety to yield an $R_2$ group selected from the groups recited above.

The cyclic hydrosiloxane compound and the compounds containing at least one unsaturated carbon-carbon bond are reacted in a hydrosilylation reaction in the presence of a suitable catalyst, such as a platinum catalyst. A wide variety of hydrosilylation catalysts have been described in the literature. U.S. Pat. No. 6,030,919 (Lewis) generally describes platinum catalysts suitable for use in hydrosilylation reactions. Suitable industrial catalysts include, but are not limited to, Speier's catalyst (chloroplatinic acid in 2-propanol), Ashby's catalyst (a platinum (0)-cyclovinylmethylsiloxane complex), and Karstedt's catalyst (a platinum (0) divinyltetramethyldisiloxane complex). The literature also cites platinum oxide (Nicolas Sabourault at al., *Organic Letters*, 4, 13, p. 2117-2119, (2002)) as well as platinum carbene complexes as effective hydrosilylation catalysts (Istvan E. Marko et al., *Science* 298, p. 204, (2002)). A variety of other metal catalysts such as those containing palladium, rhodium, ruthenium, or iridium are also known to be active for hydrosilylation (M. A. Brook, "Silicon in Organic, Organometallic, and Polymer Chemistry," pp. 401, John Wiley & Sons, 2000). Recent work has also demonstrated that hydrosilylation can be effectively catalyzed by metal complexes of non-noble metals as well (see, e.g., U.S. Pat. No. 9,073,950). In a preferred embodiment, the hydrosilylation catalyst is selected from the group consisting of Ashby's catalyst and Speier's catalyst.

The cyclic hydrosiloxane compound can be reacted with the first and second compounds comprising an acyclic, unsaturated carbon-carbon bond in any suitable order. However, the inventors have found that simultaneous addition of both the first and second compounds can lead to the production of substantial amounts of cyclic siloxane compounds containing only siloxane moieties conforming to the structure of Formula (I) or Formula (X) above. The presence of large amounts of such cyclic siloxane compounds is not desirable because the compound may not exhibit the desired combination of reactivity within an epoxy system (which is provided by the cyclic ether moiety) and compatibility or improved solubility in epoxy resins (which is provided by the —$R_{11}$-$R_{12}$ group). Thus, in one potential embodiment, the hydrosilylation of the cyclic hydrosiloxane compound is conducted by first slowly adding the first compound comprising an acyclic, unsaturated carbon-carbon bond. The addition of the first compound is then followed by controlled reaction of the resulting intermediate with the second compound comprising an acyclic, unsaturated carbon-carbon bond. For example, the resulting intermediate (produced by reaction the cyclic hydrosiloxane compound and the first compound comprising an acyclic, unsaturated carbon-carbon bond) can be added to a reaction medium containing the second compound comprising an acyclic, unsaturated carbon-carbon bond. Alternatively, the second compound comprising an acyclic, unsaturated carbon-carbon bond can be added to a reaction medium comprising the intermediate (produced by reaction the cyclic hydrosiloxane compound and the first compound comprising an acyclic, unsaturated carbon-carbon bond). This sequential and controlled reaction of the first and second compounds comprising an acyclic, unsaturated carbon-carbon bond has been found to yield a product comprising a relatively high percentage of cyclic siloxane compounds containing a combination of siloxane moieties conforming to the structure of Formula (I) and siloxane moieties conforming to the structure of Formula (X).

In a preferred embodiment of the process, the cyclic hydrosiloxane compound is first reacted with the first compound comprising an acyclic, unsaturated carbon-carbon bond. Following this hydrosilylation reaction, an acyclic hydrosiloxane compound is added to the product produced by the first hydrosilylation reaction. Following the addition of the acyclic hydrosiloxane compound, the resulting mixture of cyclic and linear hydrosiloxane compounds is reacted with the second compound comprising an acyclic, unsaturated carbon-carbon bond. Preferably, this reaction is conducted by slowly adding the mixture of cyclic and linear hydrosiloxane compounds (i.e., the mixture containing the acyclic hydrosiloxane compound and the product of the reaction between the cyclic hydrosiloxane compound and the first compound comprising an acyclic, unsaturated carbon-carbon bond) to a reaction phase containing the second compound comprising an acyclic, unsaturated carbon-carbon bond. As noted above, the reaction of the second compound with the cyclic hydrosiloxane compound yields a siloxane moiety conforming to the structure of Formula (I) in the resulting cyclic siloxane compound. Similarly, the second compound reacts with the acyclic hydrosiloxane compound to yield one or more siloxane moieties containing an $R_2$ group as described above in connection with the structure of Formula (I). The acyclic siloxane compounds conforming to the structure of Formula (L) above are examples of acyclic siloxane compounds produced by such a reaction. While not wishing to be bound to any particular theory, it is believed that an acyclic siloxane compound bearing one or more of such siloxane moieties is desirable because the $R_2$ group will react with the curative(s) used in an epoxy system. When the siloxane compound reacts with the curative, the acyclic siloxane compound will be incorporated into the cured epoxy and will not leach out or be extracted from the cured epoxy.

The acyclic hydrosiloxane compound used in such a reaction can be any suitable acyclic hydrosiloxane compound. Preferably, the acyclic hydrosiloxane compound is selected from the group consisting of compound conforms to the structure of Formula (LXX)

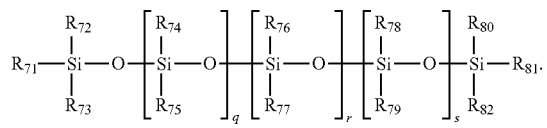

(LXX)

In the structure of Formula (LXX), $R_{71}$, $R_{72}$, $R_{73}$, $R_{74}$, $R_{75}$, $R_{76}$, $R_{77}$, $R_{78}$, $R_{79}$, $R_{80}$, $R_{81}$, and $R_{82}$ are independently selected from the group consisting of hydrogen, alkyl groups, and siloxy groups. More preferably, $R_{71}$, $R_{72}$, $R_{73}$, $R_{70}$, $R_{71}$, and $R_{72}$ are independently selected from the group consisting of alkyl groups, and $R_{74}$, $R_{75}$, $R_{76}$, $R_{77}$, $R_{78}$, and $R_{79}$ are independently selected from the group consisting of hydrogen, alkyl groups, and siloxy groups. Preferably, the alkyl groups are selected from the group consisting of $C_1$-$C_8$ alkyl groups, more preferably $C_1$-$C_4$ alkyl groups, and most preferably methyl groups. Preferably, the siloxy groups are trimethylsiloxy groups. The variables q, r, and s are independently selected from the group consisting of integers from 0 to 5, more preferably integers from 0 to 3. The sum of the variables q, r, and s preferably is from 1 to 5, more preferably from 1 to 3. Preferably, at least one of $R_{71}$, $R_{72}$, $R_{73}$, $R_{74}$, $R_{75}$, $R_{76}$, $R_{77}$, $R_{78}$, $R_{79}$, $R_{80}$, $R_{81}$, and $R_{82}$ is a hydrogen. More preferably, at least one of $R_{74}$, $R_{75}$, $R_{76}$, $R_{77}$, $R_{78}$, and $R_{79}$ is a hydrogen. In such an embodiment, the remaining groups preferably are alkyl groups, more preferably methyl groups.

The cyclic siloxane compound-containing compositions and the cyclic siloxane compounds described above are believed to be particularly well suited for use in epoxy-based thermoset resins. For example, the cyclic siloxane compounds, which contain a cyclic ether moiety (e.g., an epoxy group), can be used as the epoxy component in a two-part epoxy system. Alternatively, the cyclic siloxane compound(s) (either the composition of the first embodiment which contains cyclic siloxane compounds and/or the cyclic siloxane compound of the second embodiment) can be used in conjunction with one or more epoxy resins. In such an embodiment, any suitable epoxy resin can be used. Suitable epoxy resins are described in "Handbook of Epoxy Resins" by Henry Lee and Kris Neville (McGraw Hill Book Company, 1982 reissue), "Protective Coatings Fundamental of Chemistry and Composition" by C. H. Hare (SSPC 1994), and other references. Further, the composition of the first embodiment and/or the cyclic siloxane compound of the second embodiment can be used in conjunction with any suitable curative or combination of curatives. For example, the composition of the first embodiment and/or the cyclic siloxane compound of the second embodiment can be used in conjunction with an organic amine curative or a combination of organic amine curatives. Alternatively, the composition of the first embodiment and/or the cyclic siloxane compound of the second embodiment can be used in conjunction with an amine-containing siloxane compound as the curative.

While not wishing to be bound to any particular theory, it is believed that the compositions and the cyclic siloxane compounds described above are particularly useful in ambient temperature curing epoxy thermoset systems. For example, it is believed that an epoxy composition made with one of these compositions and/or one of these cyclic siloxane compounds can exhibit improved flexibility relative to a similar epoxy system produced without such composition(s) or cyclic siloxane compound(s). Further, it is believed that the addition of one of the compositions and/or the cyclic siloxane compounds described above can increase the water resistance and thermal stability of the cured epoxy.

Epoxies made using the composition of the first embodiment and/or the cyclic siloxane compound of the second embodiment can be used in a variety of applications. For example, such epoxies can be used as paints and coatings, such as thermally insulative coatings, corrosion prevention coatings, high temperature resistant coatings, chemical resistant coatings, release coatings, release liners, anti-fouling coatings for surfaces that come into contact with water (e.g., seawater), anti-abrasion coatings, and flexible waterproof coatings for fabrics, wood, paper, and the like. Such epoxies can also be used in bulk applications where waterproofing, flexibility, and/or improved toughness are desired. Suitable bulk applications for the epoxies include, but are not limited to, encapsulants, embedding resins, conformal coatings for electronics, waterproof coatings or potting for electrical equipment or electrical insulators, sound dampening materials, foamed epoxies (such as those used in insulation, cushioning, sound dampening, and syntactic foam), cast or molded epoxy parts, filled epoxies (e.g., epoxies filled with glass fibers or glass microspheres), and epoxy-based circuit boards. Epoxies made using the composition and/or cyclic siloxane compound of the invention can also be used in adhesives. Such epoxy adhesives can be used in wood, plastic, and/or metal laminates, attaching circuit elements to circuit boards, and other applications in which epoxy-based adhesives typically are used.

In a third embodiment, the invention provides an epoxy composition made by reacting the composition of the first embodiment described above with an epoxy resin and a curative. In this third embodiment, the cyclic siloxane-containing composition can be any of the cyclic siloxane-containing compositions described above in connection with the first embodiment of the invention. Thus, at least a portion of the cyclic siloxane compounds present in the composition comprise a first siloxane moiety and a second siloxane moiety as described above. In one preferred embodiment, the first siloxane moiety conforms to the structure of Formula (I) and the second siloxane moiety conforms to the structure of Formula (X), as each such structure is described above. Thus, in a more specific of example of such a preferred embodiment, the cyclic siloxane-containing composition preferably comprises a cyclic siloxane compound conforming to the structure of Formula (IA) described above. In such preferred embodiments, the groups $R_1$, $R_2$, $R_{10}$, $R_{11}$, and $R_{12}$ and the variables a and b can be selected from any of the groups described above in connection with the discussion of the first embodiment of the invention. Further, the cyclic siloxane-containing composition utilized in this third embodiment can comprise acyclic siloxane compounds as described above in connection with the first embodiment. In a preferred embodiment, the cyclic siloxane-containing composition comprises at least one acyclic siloxane compound conforming to the structure of Formula (L) as described above.

In a fourth embodiment, the invention provides an epoxy composition made by reacting the cyclic siloxane compound of the second embodiment as described above with an epoxy resin and a curative. In this fourth embodiment, the cyclic siloxane-containing composition can be any of the cyclic siloxane compounds described above in connection with the second embodiment of the invention. Thus, in a preferred embodiment, the cyclic siloxane compound comprises a first siloxane moiety and a second siloxane moiety, with the first siloxane moiety conforming to the structure of Formula (C) and the second siloxane moiety conforming to the structure of Formula (CX), as each such structure is described above. Thus, in a more specific of example of such a preferred embodiment, the cyclic siloxane compound preferably conforms to the structure of Formula (CA) described above. In such preferred embodiments, the groups $R_{101}$, $R_{102}$, $R_{110}$, $R_{111}$, and $R_{112}$ and the variables e and f can be selected from any of the groups described above in connection with the discussion of the second embodiment of the invention. Furthermore, in this fourth embodiment, the cyclic siloxane compound can be used in combination with an acyclic siloxane compound as described above in connection with the second embodiment of the invention. In a preferred embodiment, the cyclic siloxane compound is used in combination with at least one acyclic siloxane compound conforming to the structure of Formula (L) as described above.

Any suitable epoxy resin can be used to produce the above-described epoxy resin compositions. Suitable epoxy resins are described in "Handbook of Epoxy Resins" by Henry Lee and Kris Neville (McGraw Hill Book Company, 1982 reissue), "Protective Coatings Fundamental of Chemistry and Composition" by C. H. Hare (SSPC 1994), and other references. Suitable epoxy resins include, but are not limited to, bisphenol epoxy resins, novolac epoxy resins, glycidyl epoxy resins (e.g., aliphatic glycidyl ethers and esters and cycloaliphatic glycidyl ethers), cycloaliphatic epoxides, glycidylamine epoxy resins, and mixtures thereof. In a preferred embodiment, the epoxy resin is selected from the group consisting of bisphenol epoxy resins, novolac epoxy resins, glycidyl epoxy resins, cycloaliphatic epoxides, glycidylamine epoxy resins, and mixtures thereof.

Specific examples of epoxy resins suitable for use in the invention include multifunctional phenol novolak epoxy resins (synthesized by reacting phenol novolak with epichlorohydrin,) cresol novolak epoxy resins, and bisphenol A novolak epoxy resins. Examples of commercially available multifunctional glycidyl ether epoxy resins include those epoxy resins having the tradenames Epon 1050, Epon 160, Epon 164, Epon 1031, Epon SU-2.5, Epon SU-3, and Epon SU-8, available from Hexion Specialty Chemicals (Columbus, Ohio). Examples of commercially available multifunctional glycidyl ether epoxy resins also include the "DEN" series of epoxy resins available from Dow Chemical Co. (Midland, Mich.).

Bisphenol epoxy resins suitable for use in the composition include, but are not limited to, those conforming to the structure of Formula (CCC)

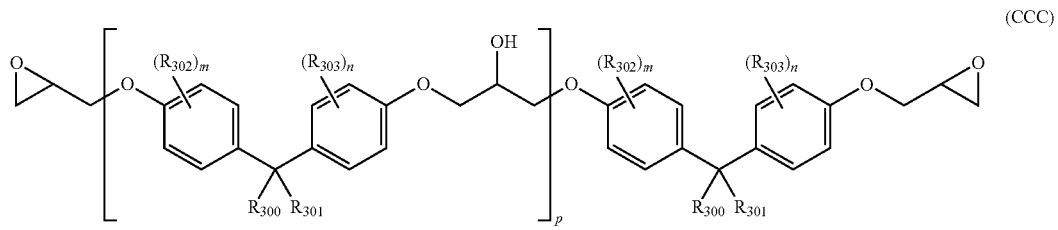

(CCC)

In the structure of Formula (CCC), $R_{300}$ and $R_{301}$ are independently selected from the group consisting of hydrogen, alkyl groups, haloalkyl groups, and aryl groups. $R_{102}$ and $R_{103}$ are independently selected from the group consisting of halogen, alkyl groups, and aryl groups. The variables m and n are independently selected from the group consisting of 0, 1, and 2; and the variable p is selected from the group consisting of integers from 0 to 50, more preferably integers from 0 to 25. Suitable commercial examples of these epoxy resins are available from Momentive (formerly Hexion) under the tradename "Epon", The Dow Chemical Company under the tradename "D.E.R.," and Huntsman Corporation's Advanced Materials business unit under the tradename "Araldite." Examples of suitable epoxy resins that are diglycidyl ethers of bisphenol A include, but are not limited to, those having the tradenames: Epon Resins 825, 826, and 828 (available from Hexion Specialty Chemicals); D.E.R. 330, 331, and 332 resins (available from Dow Chemical Co.); and Araldite GY 6008, GY 6010, and GY 2600 resins (available from Ciba Specialty Chemicals, Tarrytown, N.Y.). Examples of suitable epoxy resins that are diglycidyl ethers of bisphenol F include, but are not limited to, those having the tradenames: EPON Resin 862 resin (available from Hexion Specialty Chemicals); and Araldite GY 281, GY 282, GY 285, PY 306, and PY 307 resins (available from Ciba Specialty Chemicals).

Novolac epoxy resins suitable for use in the composition include, but are not limited to, those conforming to the structure of Formula (CCCX)

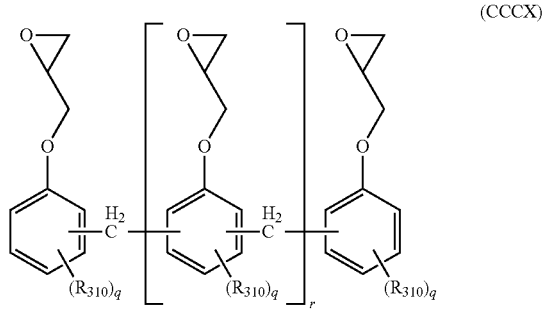

(CCCX)

In the structure of Formula (CCCX), $R_{310}$ is selected from the group consisting of halogen, alkyl groups, haloalkyl groups, and aryl groups. The variable q is selected from the group consisting of 0, 1, and 2; and the variable r is selected from the group consisting of integers from 0 to 50, more preferably integers from 0 to 25. Suitable commercial examples of these resins are available from The Dow Chemical Company under the tradename "D.E.N.™," and Huntsman Corporation's Advanced Materials business unit under the tradename "Araldite."

Suitable epoxy resins also include those derived from the poly-addition of dicyclopentadiene and phenol, which epoxy resins conform to the structure of Formula (CCCXV)

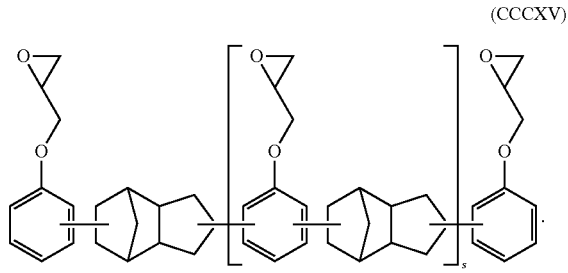

(CCCXV)

In the structure of Formula (CCCXV), the variable s is selected from the group consisting of integers from 0 to 50, more preferably integers from 0 to 25. Suitable commercial examples of these resins are available from Huntsman Chemical (East Lansing, Mich.) under the tradename "Tactix," such as the Tactix 756 and Tactix 556 epoxy resins.

Cycloaliphatic glycidyl ether epoxy resins suitable for use in the composition include, but are not limited to, those conforming to the structure of Formula (CCCXX)

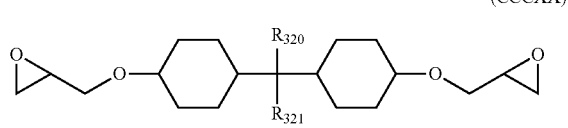

(CCCXX)

In the structure of Formula (CCCXX), $R_{320}$ and $R_{321}$ are independently selected from the group consisting of hydrogen, alkyl groups, haloalkyl groups, and aryl groups. Suitable commercial examples of these materials are believed to be available from CVC Thermoset Specialties under the tradename "Epalloy™," from New Japan Chemical Company, Ltd. under the tradename "Rikaresin HBE-100," and from Adeka USA Corporation under the tradename "Adeka Resin 4080."

Further examples of epoxy resins suitable for use in the epoxy compositions of the invention include glycidyl amine epoxy resins. Suitable examples of glycidyl amine epoxy resins include, but are not limited to, triglycidyl-p-aminophenol (also known as 4-glycidyloxy-N,N-diglycidylaniline), N,N,N',N'-tetraglycidyl-4,4-methylenebis benzylamine (also known as 4,4'-Methylenebis(N,N-diglycidylaniline)), and N,N,N',N'-tetraglycidyl-m-xylenediamine. Suitable commercial examples of glycidyl amine epoxy resins include, but are not limited to, the ERISYS™ GE resins available from CVC Thermoset Specialties and the TETRAD® X resins available from Mitsubishi Gas Chemical Company, Inc.

The epoxy resin can have any suitable epoxy equivalent weight. Preferably, the epoxy resin has an epoxy equivalent weight of about 170 g/eq. to about 500 g/eq., about 170 g/eq. to about 350 g/eq., or about 170 g/eq. to about 250 g/eq. The epoxy resin can have an average functionality of from about 1.5 to about 10.

As noted above, the epoxy composition is made by reacting the cyclic siloxane compound with an epoxy resin and a curative. The curative used can be any curative typically used in the production of epoxy compositions. Suitable curatives include, but are not limited to, organic amines, anhydrides, alcohols (e.g., phenols), thiols, and mixtures thereof. Preferably, the additional curative is selected from the group consisting of organic amines. Suitable organic amines include, but are not limited to, isophorone diamine, diethylenetriamine, triethylenetetramine, and mixtures thereof.

In the third and fourth embodiments, the combination of components reacted to produce the epoxy resin composition can further comprise a second siloxane compound. In certain embodiments, the second siloxane compound preferably is an amine-containing siloxane compound. More preferably, the second siloxane compound comprises at least two amine groups selected from the group consisting of primary amine groups and secondary amine groups. Most preferably, the second siloxane compound is an amine-terminated, substantially linear siloxane compound. In one specific preferred embodiment, the second siloxane compound is an amine-terminated, substantially linear siloxane compound comprising a plurality of siloxane moieties, wherein:

(a) a portion of the siloxane moieties are independently selected from the group consisting of siloxane moieties conforming to the structure of Formula (CC)

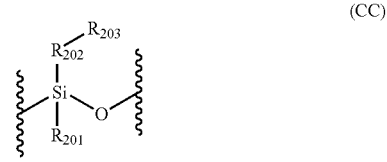

(CC)

wherein $R_{201}$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups; $R_{202}$ is selected from the group consisting of alkanediyl groups and alkenediyl groups; and $R_{203}$ is selected from the group consisting of aryl groups, substituted aryl groups, heteroaryl groups, and substituted heteroaryl groups;

(b) a portion of the siloxane moieties are independently selected from the group consisting of siloxane moieties conforming to the structure of Formula (CCX)

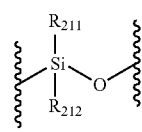

(CCX)

wherein $R_{211}$ and $R_{212}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups; and (c) the amine-terminated, substantially linear siloxane compound comprises terminal groups conforming to the structure of Formula (CCXX) and Formula (CCXXI)

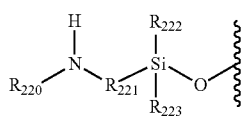

(CCXX)

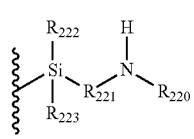

(CCXXI)

wherein $R_{220}$ is selected from the group consisting of hydrogen, alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups; $R_{221}$ is selected from the group consisting of alkanediyl groups and substituted alkanediyl groups; $R_{222}$ and $R_{223}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups. Such amine-terminated, substantially linear siloxane compounds and processes for making the same are described in more detail in U.S. Patent Application Publication No. US 2014/0296379 A1 (Christiano et al.), the disclosure of which is hereby incorporated by reference.

The siloxane repeating units conforming to the structure of Formula (CC) can constitute any suitable amount of the siloxane repeating units in the amine-terminated, substantially linear siloxane compound. While not wishing to be bound to any particular theory, it is believed that the siloxane repeating units conforming to the structure of Formula (CC), which have a pendant aromatic ring, help to make the amine-terminated, substantially linear siloxane compound more compatible with or soluble in epoxy resin systems. This improved compatibility with or solubility in epoxy resin systems minimizes or eliminates phase separation between the epoxy resin and the amine-terminated, substantially linear siloxane compound. As understood by those familiar with the art, phase separation between components in the epoxy resin system can negatively affect reactivity and curing of the resin and can also create flaws in a cured epoxy coating or a cured epoxy cast part. Thus, in order bring about this improved compatibility and solubility, the siloxane repeating units conforming to Formula (CC) preferably constitute an appreciable amount of the siloxane repeating units in the compound. Preferably, the siloxane repeating units conforming to the structure of Formula (CC) comprise about 1% or more, more preferably about 5% or more, of the siloxane repeating units in the amine-terminated, substantially linear siloxane compound. The amount of the siloxane repeating units conforming to the structure of Formula (CC) can alternatively be expressed in terms of the percentage of the siloxane compound's molecular weight that these specific repeating units constitute. More preferably, the siloxane repeating units conforming to the structure of Formula (CC) in the amine-terminated, substantially linear siloxane compound comprise about 15% or more, more preferably about 20% or more, of the molecular weight of the amine-terminated, substantially linear siloxane compound. While it is preferred for the siloxane compound to comprise an appreciable amount of siloxane repeating units conforming to the structure of Formula (CC), it is believed that there are upper limits to the amount of such repeating units that are desirable for the compound. Thus, the siloxane repeating units conforming to the structure of Formula (CC) in the amine-terminated, substantially linear siloxane compound preferably comprise about 60% or less, more preferably about 50% or less, of the molecular weight of the amine-terminated, substantially linear siloxane compound. Accordingly, in one specific preferred embodiment, the siloxane repeating units conforming to the structure of Formula (CC) in the amine-terminated, substantially linear siloxane compound comprise about 15% to about 50% of the molecular weight of the amine-terminated, substantially linear siloxane compound.

The amine-terminated, substantially linear siloxane compound can contain any suitable number of siloxane repeating units. Preferably, the total number of siloxane repeating units in the amine-terminated, substantially linear siloxane compound is about 500 or less, about 400 or less, about 300 or less, about 200 or less, about 100 or less, about 50 or less, about 40 or less, about 30 or less, about 25 or less, about 20 or less, about 15 or less, or about 10 or less. In another preferred embodiment, the total number of siloxane repeating units in the amine-terminated, substantially linear siloxane compound is about 3 or more, about 4 or more, or about 5 or more. Thus, in certain possibly preferred embodiments, the total number of siloxane repeating units in the amine-terminated, substantially linear siloxane compound is about 3 to about 500 (e.g., about 3 to about 400, about 3 to about 300, about 3 to about 200, about 3 to about 100, about 3 to about 50, about 3 to about 40 or less, about 3 to about 30 or less, about 3 to about 25 or less, about 3 to about 20 or less, about 3 to about 15 or less, or about 3 to about 10 or less), about 4 to about 500 (e.g., about 4 to about 400, about 4 to about 300, about 4 to about 200, about 4 to about 100, about 4 to about 50, about 4 to about 40 or less, about 4 to about 30 or less, about 4 to about 25 or less, about 4 to about 20 or less, about 4 to about 15 or less, or about 4 to about 10 or less), or about 5 to about 500 (e.g., about 5 to about 400, about 5 to about 300, about 5 to about 200, about 5 to about 100, about 5 to about 50, about 5 to about 40 or less, about 5 to about 30 or less, about 5 to about 25 or less, about 5 to about 20 or less, about 5 to about 15 or less, or about 5 to about 10 or less).

As noted above, the amine-terminated, substantially linear siloxane compound comprises terminal groups that preferably comprise at least one primary or secondary amine group. As demonstrated by the structures of Formulae (CCXX) and (CCXXI), these terminal groups can comprise more than one such amine group. Preferably, the number and type of amine groups present on the amine-terminated, substantially linear siloxane compound is sufficient to yield a compound exhibiting an amine hydrogen equivalent weight of about 8,000 g/eq. or less. More preferably, the amine-terminated, substantially linear siloxane compound exhibits an amine hydrogen equivalent weight of about 7,000 g/eq. or less, about 6,000 g/eq. or less, about 5,000 g/eq. or less, about 4,000 g/eq. or less, about 3,000 g/eq. or less, about 2,000 g/eq. or less, about 1,000 g/eq. or less, about 750 g/eq. or less, about 500 g/eq. or less, about 400 g/eq. or less, or about 300 g/eq. or less.

In a preferred embodiment, $R_{201}$ is selected from the group consisting of alkyl groups, preferably $C_1$-$C_{30}$ alkyl groups and more preferably $C_1$-$C_8$ alkyl groups. In a particularly preferred embodiment, $R_{201}$ is a methyl group.

Preferably, $R_{202}$ is selected from the group consisting of $C_1$-$C_{30}$ alkanediyl groups and $C_1$-$C_{30}$ alkenediyl groups, more preferably $C_1$-$C_8$ alkanediyl groups and $C_1$-$C_8$ alkenediyl groups. More preferably, $R_{202}$ is a $C_1$-$C_{30}$ alkanediyl group, most preferably a $C_1$-$C_8$ alkanediyl group. In a particularly preferred embodiment, $R_{202}$ is 2-methylethane-1,2-diyl.

In another preferred embodiment, $R_{203}$ is selected from the group consisting of aryl groups, preferably $C_6$-$C_{10}$ aryl groups. In a particularly preferred embodiment, $R_{203}$ is phenyl.

In a preferred embodiment, $R_{211}$ and $R_{212}$ are independently selected from the group consisting of alkyl groups, preferably $C_1$-$C_{30}$ alkyl groups and more preferably $C_1$-$C_8$ alkyl groups. In a particularly preferred embodiment, $R_{211}$ and $R_{212}$ are methyl groups.

Preferably, $R_{220}$ is selected from the group consisting of hydrogen, alkyl groups (e.g., $C_1$-$C_{30}$ alkyl groups), and aminoalkyl groups (e.g., $C_1$-$C_{30}$ aminoalkyl groups). More preferably, $R_{220}$ is selected from the group consisting of hydrogen, $C_1$-$C_8$ alkyl groups, and $C_1$-$C_8$ aminoalkyl groups. In one preferred embodiment, $R_{220}$ is selected from the group consisting of hydrogen and aminoalkyl groups (e.g., $C_1$-$C_8$ aminoalkyl groups). Examples of preferred aminoalkyl groups for such embodiments are aminomethyl, 2-aminoethyl, and 3-aminopropyl.

In another preferred embodiment, $R_{221}$ is selected from the group consisting of $C_1$-$C_{30}$ alkanediyl groups (e.g., $C_1$-$C_8$ alkanediyl groups) and $C_1$-$C_{30}$ substituted alkanediyl groups (e.g., $C_1$-$C_8$ substituted alkanediyl groups). More preferably, $R_{221}$ is selected from the group consisting of $C_1$-$C_8$ alkanediyl groups and $C_1$-$C_8$ substituted alkanediyl groups. Examples of preferred groups for such embodiments are ethane-1,2-diyl, propane-1,3-diyl, —CH$_2$CH(OH)CH$_2$OCH$_2$CH$_2$CH$_2$—, and —CH$_2$CH(CH$_2$OH)OCH$_2$CH$_2$CH$_2$—.

In a preferred embodiment, $R_{222}$ and $R_{223}$ are independently selected from the group consisting of alkyl groups, preferably $C_1$-$C_{30}$ alkyl groups, and more preferably $C_1$-$C_8$ alkyl groups. In a particularly preferred embodiment, $R_{222}$ and $R_{223}$ are methyl groups.

In another preferred embodiment, $R_{201}$, $R_{211}$, $R_{212}$, $R_{222}$, and $R_{223}$ are selected from the group consisting of alkyl groups. More preferably, $R_{201}$, $R_{211}$, $R_{212}$, $R_{222}$, and $R_{223}$ are methyl groups. In another preferred embodiment, $R_{202}$ is 2-methylethane-1,2-diyl, and $R_{203}$ is phenyl. Thus, in a particularly preferred embodiment, $R_{201}$, $R_{211}$, $R_{212}$, $R_{222}$, and $R_{223}$ are methyl groups, $R_{202}$ is 2-methylethane-1,2-diyl, and $R_{203}$ is phenyl.

The epoxy compositions of the third and fourth embodiment can be produced using any suitable relative amounts of the cyclic siloxane-containing composition or cyclic siloxane compound, epoxy resin(s), curative(s), and amine-containing siloxane compound (if present). As will be understood by those of ordinary skill in the art, the desired relative amount of each component will depend, at least in part, upon the desired properties of the cured epoxy composition. Preferably, the siloxane compounds comprise about 10 wt. % or more of the reactants used to produce the epoxy composition. Further, if an amine-containing siloxane compound is used to produce the epoxy composition, the mass ratio of the cyclic siloxane compound to the amine-containing siloxane compound preferably is about 50:1 or less, about 25:1 or less, or about 10:1 or less. As will be understood by those of ordinary skill in the art, the targeted stoichiometry for the epoxy composition will also be based on the ratio of total epoxy equivalents (contributed by the siloxane compounds and any epoxy resins(s)) to total amine hydrogen equivalents (contributed by the amine curative(s) and amine-containing siloxane compounds (if present)). One approach is to add sufficient amounts of each component to yield a ratio of total epoxy equivalents to amine hydrogen equivalents of about 1:1. Alternatively, the amounts of the components can be varied to yield a ration of total epoxy equivalents to amine hydrogen equivalents from about 5:1 to about 1:2. The desired ratio within this range will depend, at least in part, on the desired final properties of the epoxy composition.

As will be understood by those skilled in the art, the combination of components described in the third and fourth embodiment, which comprise a cyclic siloxane compound comprising a cyclic ether moiety and an epoxy curative, contain components that will react to form a cured epoxy. Thus, upon combining the individual components of the composition at ambient temperatures, the cyclic siloxane compound and the epoxy curative will begin to react. Given sufficient time, the composition will cure to yield a cured epoxy in which the cured polymer contains segments derived from the cyclic siloxane compound and the epoxy curative. Further, if the composition contains an epoxy resin in addition to the cyclic siloxane compound described herein and/or another curative in addition to the epoxy curative described above (e.g., an amine-containing siloxane compound), the cured epoxy polymer will also contains segments derived from the epoxy resin and/or the additional curative.

The following examples further illustrate the subject matter described above but, of course, should not be construed as in any way limiting the scope thereof.

The distribution of different cyclic siloxane species produced in the following examples was determined using high-performance liquid chromatography-mass spectrometry (HPLC-MS). In particular, a 10 μL aliquot of the sample was dissolved in 1 mL of tetrahydrofuran (THF) containing 250 ppm butylated hydroxytoluene as a stabilizer. The sample was injected into a Waters Alliance 2965 HPLC system with a 2.1×150 mm, 5 μm ZORBAX Eclipse XDB-C18 column and a C18 guard column. The mobile phase consisted of stabilizer-free THF ("Mobile Phase A"), methanol ("Mobile Phase B"), and water ("Mobile Phase C"). Elution was performed at 30° C. using a flow rate of 0.3 mL/min and the mobile phase gradient in Table 1 below. All gradient changes were linear. Separation was monitored by a Waters 2996 photodiode array detector scanning wavelengths from 200 to 800 nm and a Waters Micromass ZQ quadrupole mass spectrometer equipped with an electrospray ionization (ESI) source. The ESI source was set to positive mode scanning an m/z range from 100 to 2,000 with a capillary voltage of 3.4 kV, a cone voltage of 10 V, a source temperature of 130° C. and a desolvation temperature of 400° C.

TABLE 1

Mobile Phase Gradient for HPLC-MS analysis

| Time (min) | Mobile Phase A | Mobile Phase B | Mobile Phase C |
|---|---|---|---|
| 0 | 0% | 65% | 35% |
| 3 | 0% | 75% | 25% |
| 13 | 0% | 100% | 0% |
| 18 | 0% | 100% | 0% |
| 25 | 20% | 80% | 0% |
| 30 | 20% | 80% | 0% |
| 35 | 0% | 100% | 0% |
| 45 | 0% | 100% | 0% |
| 50 | 0% | 65% | 35% |
| 60 | 0% | 65% | 35% |

Calculation of the product ratios was performed by extracting ion chromatograms of the signals that correspond to the $[M+H_2O]^+$ and $[M+Na]^+$ ions of the species present and integrating the peak area for each detected species. The area percent for each peak was calculated based on the total sum of the separately integrated peaks.

EXAMPLE 1

This example demonstrates the production of a cyclic siloxane compound and a composition according to the invention.

222.57 g (0.925 moles, 3.70 equivalents) of tetramethylcyclotetrasiloxane (SiVance, LLC) was added to a one liter round bottom reaction vessel fitted with a Claisen adapter with a thermocouple, a pressure compensating addition funnel, a condenser fitted with an air flow adapter, and a mechanical stirrer. The thermocouple was connected to a temperature control unit controlling a heating mantle under the flask. The setup was purged with dry nitrogen gas and then brought up to 75° C. Approximately 818 μL of Ashby's catalyst containing 2 wt. % Pt (SiVance) was added to the reaction vessel, and approximately 185.81 g (1.57 mole) of α-methylstyrene (Aldrich) was slowly added from the addition funnel. As the reaction proceeded, excess heat was removed by replacing the heating mantle with a cooling bath to maintain temperature below 95° C. The reaction was held at a temperature of about 85° C. using the heating mantle for 2 hours. $^1$H NMR was used to assess utilization of SiH, showing about 42% utilization of cyclic SiH equivalents through reaction with α-methylstyrene. Then, approximately 290.9 g (2.55 mole) of allyl glycidyl ether (Aldrich) was slowly added to the reaction mixture in the vessel from the addition funnel, while maintaining a temperature of about 85° C. After the addition of the allyl glycidyl ether was complete, the temperature of the resulting mixture was raised to approximately 105° C. and held at temperature for about 2 hours. A sample was collected and tested for SiH content using $^1$H NMR. The SiH content was found to be reduced by greater than 99% in comparison to a reference mixture containing tetramethylcyclotetrasiloxane, α-methylstyrene, and allyl gylcidyl ether in the ratio of masses added to the reaction mixture. The reaction mixture was then stripped under vacuum using progressively hotter temperatures up to 166° C. The final product was an amber colored liquid with an epoxy equivalent weight of 311 g/equivalent, and a viscosity (25° C.) of 210 cP. $^{29}$Si NMR confirmed the presence of two different diorganosiloxane species consistent with formation of a glycidoxy propyl methyl siloxy moiety and a phenylpropyl methyl siloxy moiety. The final product was also analyzed by HPLC-MS according to the procedure described above in order to assess the distribution of different cyclic siloxane compounds in the resulting product. The results of the HPLC-MS are set forth in Table 1 below. In the table, the different cyclic siloxane compounds are grouped by the number of glycidoxy propyl methyl siloxy moieties (labelled "AGE" in the table) and phenylpropyl methyl siloxy moieties (labelled "AMS" in the table) present in the compound. One group of cyclic siloxane compounds also contained a silanol group, which group is designated as "SiOH" in the table below.

TABLE 2

Distribution of different cyclic siloxane compounds in the product of Example 1.

| Compound | Selected Mass | Peak Area (%) |
|---|---|---|
| 4 AGE | 714 | 36.3 |
| 3 AGE, 1 AMS | 718 | 32.0 |
| 2 AGE, 2 AMS | 723 | 25.4 |
| 1 AGE, 2 AMS, SiOH | 609 | 0.4 |
| 1 AGE, 3 AMS | 726 | 5.9 |
| 4 AMS | 730 | 0.0 |

As can be seen from the data shown in Table 2, the product of the reaction is a mixture of several different cyclic siloxane compounds. Further, the data show that over 60 percent of the compounds in the composition comprise at least one glycidoxy propyl methyl siloxy moiety (AGE) and at least one phenylpropyl methyl siloxy moiety (AMS). While the composition comprises an appreciable amount (36%) of compounds comprising only glycidoxy propyl methyl siloxy moieties (AGE), the presence of such compounds is not problematic because the cyclic ether in the moiety will react with curative(s) used in an epoxy system, thereby allowing these compounds to be incorporated into the cured epoxy. The data also show that the composition does not contain a detectable amount of compounds comprising only phenylpropyl methyl siloxy moieties (AMS). As is explained above, the presence of appreciable amounts of such compounds is not desirable because the compound does not contain any groups that are reactive in an epoxy system. Therefore, the compound is not capable of being chemically incorporated into the cured epoxy. And such compounds may leach out of the cured epoxy or their presence may affect the properties (e.g., strength) of the cured epoxy.

EXAMPLE 2

This example demonstrates the production of a composition comprising cyclic siloxane compounds according to a method described in U.S. Pat. No. 7,777,064 (Mizori).

In particular, a reaction was run in an attempt to replicate the method and yield the product described in Example 5 of U.S. Pat. No. 7,777,064. The reaction was run in a 500 mL 3 necked round bottom flask fitted with a magnetic stir bar, a condenser/air flow adapter, a 24/40 stopper, and a Claisen adapter with a temperature probe and a side arm addition funnel. Approximately 20.04 g (83.2 mmol, 333 milliequivalents) of tetramethylcyclotetrasiloxane (SiVance) and approximately 144.92 grams of toluene (HPLC grade) were added to the round bottom flask. Next, approximately 25.45 g of allyl glycidyl ether (Yokkaichi) (223 mmol) was added to the addition funnel. The reaction was heated to a temperature of approximately 50° C. with mixing and then 4 particles (0.0287 g, 10.6 mg as Pt) of chloroplatinic acid hexahydrate were added to the reaction vessel using a spatula. Approximately 5.5 g of toluene was used to wash any chloroplatinic acid particles from the spatula into the reaction vessel. Upon addition of the catalyst, the addition of allyl glycidyl ether to the round bottom flask was initiated at a slow dropwise rate of addition. The reaction showed an exotherm and the heating mantle was turned off and removed to allow the flask to cool in the air. Under air cooling, the reaction mixture reached a temperature of about 75° C. The addition of the allyl glycidyl ether was completed in about 17 minutes. After the exotherm subsided and the reaction mixture returned to a temperature of approximately 50° C., approximately 14.83 g (110 mmol) of 2-allyl phenol was placed in the addition funnel and slowly added to the round bottom flask addition by dropwise addition. Another exotherm raised the temperature of the reaction mixture to approximately 75° C. The addition of the 2-allyl phenol was completed in about 13 minutes. The reaction was held at a temperature of approximately 70° C. overnight. The next morning, the toluene solvent and any unreacted volatile material was removed by vacuum distillation at a temperature of approximately 60° C. with the stripping stopped after the bubbling ceased. The resulting brown liquid product was then analyzed by HPLC-MS according to the procedure described above. The HPLC-MS analysis revealed a mixture of several different cyclic siloxane compounds. These species were identified by mass and are listed in the table below by the moieties attached to the silxoane ring. In the table, a glycidoxy propyl methyl siloxy moiety is designated by the abbreviation "AGE," a phenol propyl siloxy moiety is designated by the abbreviation "APOH," a silanol group is designated by the abbreviation "SiOH," and a hydrosiloxy moiety is designated by the abbreviation "SiH."

TABLE 3

Distribution of the different cyclic siloxane compounds in the product of Example 2.

| Compound | Peak Area (%) |
|---|---|
| 4 AGE | 30 |
| 3 AGE, 1 SiH | 3 |
| 3 AGE, 1 SiOH | 28 |
| 3 AGE, 1 APOH | 17 |
| 2 AGE, 1 APOH, 1 SiOH | 11 |
| 1 AGE, 2 APOH, 1 SiOH | 1 |
| 3 APOH, 1 SiOH | 4 |

As can be seen from the data in Table 3, the product contains a mixture of several different cyclic siloxane compounds. Example 5 of U.S. Pat. No. 7,777,064 states that the target compound was a D4 cyclic siloxane containing two AGE moieties and two APOH moieties. However, the HPLC analysis shows that no detectable amounts of this target compound were produced using the reaction conditions described in U.S. Pat. No. 7,777,064. Indeed, only a relatively minor percentage (less than 30%) of the compounds in the product comprise at least one AGE moiety and at least one APOH moiety.

EXAMPLE 3

This example demonstrates the production of two cyclic siloxane compound-containing compositions according to the invention. The example also demonstrates the effects of including an acyclic siloxane compound in a composition according to the invention.

Two cyclic siloxane compound-containing compositions (Samples 3A and 3B) were synthesized using the following general procedure. The amount of each reactant used in producing each composition is set forth in Table 4 below. A one liter round-bottom reaction flask was equipped with a heating mantle, a mechanical stirrer, a small (50 ml) addition funnel, a metering pump for olefin addition, a temperature probe, reflux condenser, and nitrogen sweep. The tetramethylcyclosiloxane, heptamethyltrisiloxane (if used), and 15 grams of α-methylstyrene were charged to the reaction flask and blanketed by nitrogen. The contents of the flask were heated to approximately 95° C. with moderate agitation. Approximately 2.0 milliliters of freshly prepared Speier's Catalyst (300 milligrams of chloroplatinic acid in 10.0 grams of anhydrous isopropanol) were added to the reaction mixture. A pronounced exotherm was observed indicating the successful initiation of the hydrosilylation reaction. The remaining α-methylstyrene was then metered into the reaction mixture at a rate of about 2 milliliters per minute. The temperature of the reaction mixture was maintained at 95° C. to 100° C. by applying cooling and/or by slowing the rate of addition. After the α-methylstyrene addition was complete, the reaction mixture was held at approximately 95° C. for approximately 15 minutes to ensure complete reaction and then cooled to a temperature of less than 40° C. This product ("AMS intermediate") was then transferred to a one quart glass bottle and maintained under dry nitrogen. Then, approximately 245 grams of allyl glycidyl ether was charged to the reaction flask along with approximately 1.0 milliliters of the Speier's Catalyst solution. The temperature of the reaction vessel was raised to approximately 80° C., and the AMS Intermediate was added at a rate of about 6 milliliters per minute over a time of about one hour. The temperature of the reaction mixture was maintained between 85° C. and 90° C. by applying cooling as required. After the addition of the AMS Intermediate was complete, the temperature of the reaction mixture was maintained at 75° C. to 85° C. FTIR analysis was used to determine when the SiH was completely consumed. Once all of the SiH was consumed, approximately 3.0 grams of MgO powder was charged to the reaction mixture while maintaining a temperature of 85° C. The resulting mixture was vacuum stripped with a nitrogen sparge while slowly raising the temperature to approximately 130° C. to remove any volatiles. The mixture was cooled to a temperature below 40° C. and filtered to remove solids from the liquid product.

TABLE 4

Reactants and amounts used in the synthesis of Samples 3A and 3B.

| Reactant | Sample 3A | Sample 3B |
|---|---|---|
| tetramethylcyclotetrasiloxane | 180 g | 160 g |
| α-methylstyrene | 145 g | 145 g |
| Speier's Catalyst | 3.0 mL | 3.0 mL |
| heptamethyltrisiloxane | 0 g | 20 g |
| allyl glycidyl ether | 245 g | 245 g |

The viscosity of each product was measured at a temperature of 25° C. The viscosity of Sample 3A was 600 cP, and the viscosity of Sample 3B was 200 cP. Thus, the inclusion of a relatively minor amount of acyclic siloxane compounds (approximately a 6:1 ratio of cyclic siloxane compounds to acyclic siloxane compounds) reduced the viscosity of the composition to one third of the viscosity of a similar composition that did not include the acyclic siloxane compound. These data shows how the inclusion of an acyclic siloxane compound can be used to lower the viscosity of the composition, which could facilitate incorporation of the composition into lower viscosity epoxy resins.

EXAMPLE 4

This example demonstrates the production of another composition according to the invention.

A two liter three-necked, round-bottom reaction flask was equipped with a heating mantle, a mechanical stirrer, a small (50 ml) addition funnel, a metering pump for controlled rate of addition, a temperature probe, reflux condenser, and nitrogen sweep. Approximately 200 g of mixed methyl hydrogen cyclosiloxanes (containing a mixture of tetramethylcyclotetrasiloxane, pentamethylcyclopentasiloxane, and hexamethylcyclohexasiloxane) (3.33 equivalents of SiH) was added to the reaction flask and blanketed with nitrogen. The contents of the flask were heated to a temperature of approximately 85° C. with moderate agitation under a gentle nitrogen sweep, and 5.0 ml of a Speier's Catalyst solution was added. Then, α-methylstyrene was added at a rate of 1 mL/min using the controlled addition pump. The reaction mixture was cooled to maintain a temperature of about 95° C. to about 100° C. A total of 177 g (1.50 mol) of α-methylstyrene was added over about 3 to 4 hours. After the addition of the α-methylstyrene was completed, the reaction mixture was stirred for 60 minutes at a temperature of approximately 95° C. A sample was taken from the reaction mixture and an analysis demonstrated that the SiH content was 4.8 mmol/g, which indicated that the α-methylstyrene reaction was greater than 95% completed, utilizing about 45% of the cyclic SiH equivalents. The reaction mixture ("AMS Intermediate") was cooled to a temperature below 40° C. and transferred to a one quart glass bottle. Then, approximately 14.33 g of heptamethyltrisiloxane ("HPTSO") was added to and mixed with the AMS Intermediate ("AMS Intermediate/HPTSO mixture").

Next, approximately 138.2 g of allyl glycidyl ether was charged to the reaction vessel, providing approximately a 30% stoichiometric excess of allyl glycidyl ether. The reaction vessel was heated to a temperature of about 80° C. and 0.25 milliliters of Speier's Catalyst solution was added. Immediately after addition of the catalyst, the addition of the AMS Intermediate/HPTSO was initiated. Approximately 200 g of the AMS Intermediate/HPTSO mixture was added at a controlled rate of about 2.7 ml/min over a time of about one hour. The temperature of the reaction mixture was maintained at about 85° C. to 90° C. by applying cooling or heating as required. After the addition of the AMS Intermediate/HPTSO mixture was completed, the temperature of the reaction mixture was maintained at a temperature of about 85° C. to 90° C. for approximately 30 minutes. FTIR analysis of the reaction mixture showed complete consumption of the SiH. Then, approximately 5 g of MgO powder was added with stirring while maintaining a temperature of 85° C. The resulting mixture was vacuum stripped at a temperature up to 130° C. for a minimum 3 hours to remove all residual volatiles. The stripped mixture was cooled to a temperature below 40° C. and filtered to remove solids from the liquid product. The product obtained was a transparent, nearly colorless liquid having a viscosity of 291 cP and an epoxy equivalent weight of 340 g/eq. The distribution of cyclic siloxane compounds was determined using an HPLC-MS method similar to that described above, except that the mobile phases were water, methanol, and acetonitrile. The analysis showed that the liquid product contained approximately 69% cyclic siloxane compounds containing varying numbers of AGE and AMS moieties. The results of the analysis are set forth in Table 5 below, which shows the relative amounts of the different cyclic siloxane products present in the product.

TABLE 5

Distribution of cyclic siloxane compounds in the product produced in Example 4.

| D4 Rings | |
|---|---|
| 4 AGE | 11% |
| 3 AGE 1 AMS | 12% |
| 2 AGE 2 AMS | 11% |
| 1 AGE 3 AMS | 3% |
| 4 AMS | 0% |
| D5 Rings | |
| 5 AGE | 13% |
| 4 AGE 1 AMS | 15% |
| 3 AGE 2 AMS | 20% |
| 2 AGE 3 AMS | 8% |
| 1 AGE 4 AMS | 0% |
| 5 AMS | ND |
| D6 Rings | |
| 6 AGE | 1% |
| 5 AGE 1 AMS | 1% |
| 4 AGE 2 AMS | 2% |
| 3 AGE 3 AMS | 3% |
| 2 AGE 4 AMS | 0% |
| 1 AGE 5 AMS | ND |
| 6 AMS | ND |

The results in Table 5 show that the resulting composition contains a mixture of several different cyclic siloxane compounds. The composition does not contain a detectable amount of cyclic siloxane compounds containing only AMS moieties, which as noted above are not desirable for incorporation into epoxy compositions. Further, about 75% of the cyclic siloxane compounds present in the composition contain at least one AGE moiety and at least one AMS moiety. As is explained above, such cyclic siloxane compounds are desirable because the AGE moieties enable the compounds to react into an epoxy composition and the AMS moieties improve the physical properties of the resulting epoxy composition.

EXAMPLE 5

This example demonstrates the production of an epoxy composition according to the invention.

Approximately 46 g of the composition of Example 4 (epoxy equivalent weight 310.7 g/eq.) was mixed with 77.1 g of Epalloy 7190 (a bis-phenol A epoxy resin from CVC Thermoset Specialties) and 20.0 of a reactive diluent HELOXY™ Modifier 65 (Momentive). HELOXY™ Modifier 65 is a glycidyl ether of para-tertiary butyl phenol. This mixture was combined with a curative blend containing 22.86 g of isophorone diamine and 34.0 g of C1008 Curative (a substantially linear amino siloxane curative from SiVance, LLC) to yield a mixture with a total epoxy to total amine hydrogen equivalent ratio of 1:1. The resulting mixture was blended and deaerated, and then portions were poured into molds (i.e., molds for tensile elongation testing samples) and cured at a temperature of about 70° C. for 16 hours. Additionally, a portion of the resulting mixture was poured into a 9 dram glass vial and allowed to cure 24 hours at room temperature. The sample in the glass vial was used to assess the clarity of the cured epoxy composition. The cured epoxy composition was transparent with low turbidity. Tensile testing of the molded samples showed that the samples exhibited useful properties of 4.2+/−1% elongation at break, a modulus of 1679±271 MPa, and a stress at break of 24.5±0.4 MPa.

EXAMPLE 6

This example demonstrates the production of an epoxy composition according to the invention.

Two epoxy compositions (Comparative Sample 6 and Sample 6) were produced by combining the raw materials listed in Table 6. Epalloy 7190 is a bis-phenol A epoxy available from CVC Thermoset. HELOXY™ Modifier 65 is a glycidyl ether of para-tertiary butyl phenol. Accelerator 399 is an epoxy curing promoter for use with amine hardeners available from Huntsman and is believed to contain a mixture of 1-(2-aminoethyl)piperazine, piperazine, and triethanolamine. The raw materials were combined in a Max 100 FlackTek cup, and the total mass of the combined raw materials was 60 g. The materials were then mixed using a FlackTek mixer (model DAC400.1 FVZ) at 2,300 RPM for 3 minutes prior to application to a substrate. The coating mixture was then applied to smooth finish, cold-rolled steel Q-Panels having a thickness of 0.020 inches (type QD36, from Q-Lab Corporation) that had been wiped down with reagent grade isopropyl alcohol to remove any residual oils from the surface. The coatings were applied using a Gardner Knife adjustable drawdown blade (Paul N. Gardner Company) set to deliver a 10 mil dry film thickness coating. A BYK Automatic Film Applicator (Byko-drive model 2121c) was set to apply the coating to the substrate at a speed of 10 mm per second.

TABLE 6

Raw materials and amounts used in making Comparative Sample 6 and Sample 6

| Raw Material | Source | Comparative Sample 6 | Sample 6 |
| --- | --- | --- | --- |
| Epalloy 7190 | CVC Thermoset | 69.8% | 33.1% |
| HELOXY ™ Modifier 65 | Momentive | 10.0% | 10.0% |
| Mixed glycidoxy propyl siloxy, phenylpropyl methyl siloxy cyclic siloxanes | Example 1 | 0% | 40.0% |
| Accelerator 399 | Huntsman | 3.0% | 3.0% |
| Isophorone diamine | Sigma Aldrich | 17.2% | 13.9% |

The freshly coated panels were placed in a 70° C. oven for 13 hours to cure. The panels were allowed to equilibrate to ambient conditions for 3 hours prior to performing the bending test described below.

A cylindrical mandrel bend test was performed in accordance with ASTM Standard D522 with a 180° bend time of 1 second using a TQC Model SP1820-178 cylindrical mandrel bend device. The test deviated from the conditions described in the standard in terms of substrate thickness and performing the recommended conditioning of the panels. The ambient conditions in the lab at the time the bending test was performed were approximately 22.6° C. and 66% relative humidity. All three of the panels coated with Comparative Sample 6 cracked and failed the test when bent around a 1 inch cylindrical mandrel. All three of the panels coated with Sample 6 did not crack and passed the test when bent around a ⅛ inch cylindrical mandrel. To verify that all panels had sufficiently cured, the test was repeated after allowing the panels to cure for an additional 72 hours in a 70° C. oven. The same results were obtained in this second round of bend testing.

These results demonstrate the physical property improvements that can be imparted to an epoxy composition through the incorporation of a cyclic siloxane-containing composition according to the invention. In particular, it is believed that these results demonstrate that epoxy coatings made with a cyclic siloxane-containing composition according to the invention exhibit vastly improved flexibility relative to similar epoxy coatings made without the composition.

EXAMPLE 7

This example demonstrates the production of an epoxy composition according to the invention.

A siloxane-modified, aromatic epoxy composition was prepared by combining 1.502 g of isophorone diamine co-curative with 3.016 g (20 wt. % of total) of C1008 Curative (a substantially linear amino siloxane curative from SiVance, LLC). This mixture was then combined with 5.272 g (15 wt. %) of the composition from EXAMPLE 4 and 5.247 g of Epalloy 7190 (a bis-phenol A epoxy available from CVC Thermoset) to provide a total epoxy to total amine hydrogen equivalent ratio of 0.994:1.

Molded samples were prepared by blending 6.1039 g of the resulting epoxy mixture with 40 wt. % of epoxy-modified, hollow glass spheres (H50/100000 EPX from 3M corporation) in a small plastic cup. The resulting mixture was then high shear mixed using a FlackTek mixer (model DAC 400.1 FVZ) for 45 seconds at 2,300 RPM and room temperature. The mixture was cured at room temperature to provide a solid, white molded object. After approximately 36 hours, the Shore D hardness of the object was measured, giving an average measured hardness of 66.5.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A composition comprising a plurality of cyclic siloxane compounds, at least a portion of the cyclic siloxane compounds comprising a first siloxane moiety and a second siloxane moiety, wherein:
   (a) the first siloxane moiety is selected from the group consisting of moieties conforming to the structure of Formula (I)

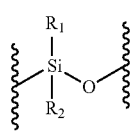

(I)

where $R_1$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups, and $R_2$ is a group comprising a cyclic ether moiety;

(b) the second siloxane moiety is selected from the group consisting of moieties conforming to the structure of Formula (X)

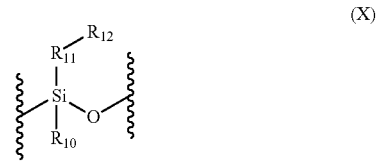

(X)

where $R_{10}$ is a methyl group; $R_{11}$ is a 2-methylethane-1,2-diyl group; and $R_{12}$ is a phenyl group; and
   (c) about 35% or more of the cyclic siloxane compounds present in the composition comprise at least one first siloxane moiety and at least one second siloxane moiety.

2. The composition of claim 1, wherein about 10% or less of the cyclic siloxane compounds present in the composition contain only second siloxane moieties.

3. The composition of claim 1, wherein $R_2$ comprises an epoxide moiety.

4. The composition of claim 1, wherein $R_2$ is a group conforming to the structure $—R_5—O—R_6$, where $R_5$ is an alkanediyl group and $R_6$ is a group comprising an epoxide moiety.

5. The composition of claim 4, wherein $R_5$ is a propane-1,3-diyl group, and $R_6$ is a glycidyl group.

6. A cyclic siloxane compound comprising a plurality of siloxane moieties, the compound comprising:
   (a) at least one first siloxane moiety conforming to the structure of Formula (C)

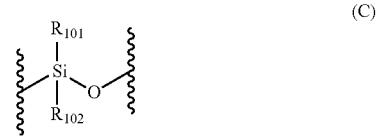

(C)

wherein $R_{101}$ is selected from the group consisting of alkyl groups; and $R_{102}$ is a group comprising a cyclic ether moiety; and
   (b) at least one second siloxane moiety conforming to the structure of Formula (CX)

(CX)

wherein $R_{110}$ is a methyl group; $R_{111}$ is a 2-methylethane-1,2-diyl group; and $R_{112}$ is a phenyl group.

7. The cyclic siloxane compound of claim 6, wherein $R_{102}$ comprises an epoxide moiety.

8. The cyclic siloxane compound of claim 6, wherein $R_{102}$ is a group conforming to the structure —$R_5$—O—$R_6$, where $R_5$ is an alkanediyl group and $R_6$ is a group comprising an epoxide moiety.

9. The cyclic siloxane compound of claim 8, wherein $R_5$ is a propane-1,3-diyl group, and $R_6$ is a glycidyl group.

10. An epoxy composition made by reacting:
(a) a composition comprising a plurality of cyclic siloxane compounds, at least a portion of the cyclic siloxane compounds comprising a first siloxane moiety and a second siloxane moiety, wherein:
    (i) the first siloxane moiety is selected from the group consisting of moieties conforming to the structure of Formula (I)

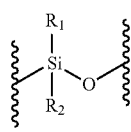

(I)

where $R_1$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups, and $R_2$ is a group comprising a cyclic ether moiety;
    (ii) the second siloxane moiety is selected from the group consisting of moieties conforming to the structure of Formula (X)

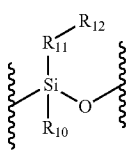

(X)

where $R_{10}$ is a methyl group; $R_{11}$ is a 2-methylethane-1,2-diyl group; and $R_{12}$ is a phenyl group and
    (iii) about 35% or more of the cyclic siloxane compounds present in the composition comprise at least one first siloxane moiety and at least one second siloxane moiety;
(b) an epoxy resin; and
(c) a curative.

11. The epoxy composition of claim 10, wherein $R_2$ comprises an epoxide moiety.

12. The epoxy composition of claim 10, wherein $R_2$ is a group conforming to the structure —$R_5$—O—$R_6$, where $R_5$ is an alkanediyl group and $R_6$ is a group comprising an epoxide moiety.

13. The epoxy composition of claim 12, wherein $R_5$ is a propane-1,3-diylgroup, and $R_6$ is a glycidyl group.

14. The epoxy composition of claim 10, wherein the epoxy composition is made by reacting the composition comprising a plurality of cyclic siloxane compounds, the epoxy resin, the curative, and a second siloxane compound, and the second siloxane compound is an amine-terminated, substantially linear siloxane compound comprising a plurality of siloxane moieties, wherein:
(a) a portion of the siloxane moieties are independently selected from the group consisting of siloxane moieties conforming to the structure of Formula (CC)

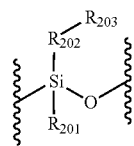

(CC)

wherein $R_{201}$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups; $R_{202}$ is selected from the group consisting of alkanediyl groups and alkenediyl groups; and $R_{203}$ is selected from the group consisting of aryl groups, substituted aryl groups, heteroaryl groups, and substituted heteroaryl groups;
(b) a portion of the siloxane moieties are independently selected from the group consisting of siloxane moieties conforming to the structure of Formula (CCX)

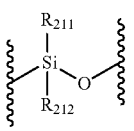

(CCX)

wherein $R_{211}$ and $R_{212}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups; and
(c) the amine-terminated, substantially linear siloxane compound comprises terminal groups conforming to the structure of Formula (CCXX) and Formula (CCXXI)

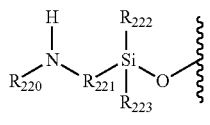

(CCXX)

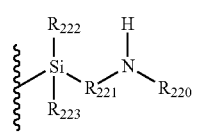

(CCXXI)

wherein $R_{220}$ is selected from the group consisting of hydrogen, alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups; $R_{221}$ is selected from the group consisting of alkanediyl groups and substituted alkanediyl groups; $R_{222}$ and $R_{223}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups.

15. An epoxy composition produced by reacting:
    (a) a cyclic siloxane compound, the cyclic siloxane compound comprising:
       (ii) at least one first siloxane moiety conforming to the structure of Formula (C)

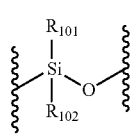

(C)

wherein $R_{101}$ is selected from the group consisting of alkyl groups; and $R_{102}$ is a group comprising a cyclic ether moiety; and
       (ii) at least one second siloxane moiety conforming to the structure of Formula (CX)

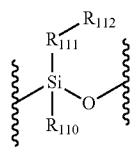

(CX)

wherein $R_{110}$ is a methyl group; $R_{111}$ is a 2-methylethane-1,2-diyl group; and $R_{112}$ is a phenyl group;
    (b) an epoxy resin; and
    (c) a curative.

16. The epoxy composition of claim 15, wherein $R_{102}$ comprises an epoxide moiety.

17. The epoxy composition of claim 15, wherein $R_{102}$ is a group conforming to the structure —$R_5$—O—$R_6$, where $R_5$ is an alkanediyl group and $R_6$ is a group comprising an epoxide moiety.

18. The epoxy composition of claim 17, wherein $R_5$ is a propane-1,3-diyl group, and $R_6$ is a glycidyl group.

19. The epoxy composition of claim 15, wherein the epoxy composition is made by reacting the cyclic siloxane compound, the epoxy resin, the curative, and a second siloxane compound, and the second siloxane compound is an amine-terminated, substantially linear siloxane compound comprising a plurality of siloxane moieties, wherein:
    (a) a portion of the siloxane moieties are independently selected from the group consisting of siloxane moieties conforming to the structure of Formula (CC)

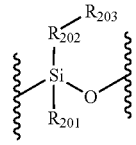

(CC)

wherein $R_{201}$ is selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups; $R_{202}$ is selected from the group consisting of alkanediyl groups and alkenediyl groups; and $R_{203}$ is selected from the group consisting of aryl groups, substituted aryl groups, heteroaryl groups, and substituted heteroaryl groups;
    (b) a portion of the siloxane moieties are independently selected from the group consisting of siloxane moieties conforming to the structure of Formula (CCX)

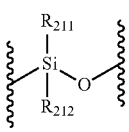

(CCX)

wherein $R_{211}$ and $R_{212}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups; and
    (c) the amine-terminated, substantially linear siloxane compound comprises terminal groups conforming to the structure of Formula (CCXX) and Formula (CCXXI)

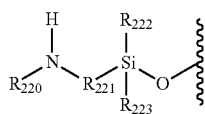

(CCXX)

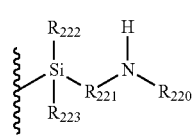

(CCXXI)

wherein $R_{220}$ is selected from the group consisting of hydrogen, alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups; $R_{221}$ is selected from the group consisting of alkanediyl groups and substituted alkanediyl groups; $R_{222}$ and $R_{223}$ are independently selected from the group consisting of alkyl groups, substituted alkyl groups, cycloalkyl groups, substituted cycloalkyl groups, alkenyl groups, substituted alkenyl groups, cycloalkenyl groups, substituted cycloalkenyl groups, heterocyclyl groups, substituted heterocyclyl groups, aryl groups, substituted aryl groups, heteroaryl groups, and substituted heteroaryl groups.

* * * * *